US009975879B2

(12) United States Patent
Abou-Gharbia et al.

(10) Patent No.: US 9,975,879 B2
(45) Date of Patent: May 22, 2018

(54) BETA LACTAMS AS MODULATORS OF GLUTAMATE UPTAKE AND METHODS FOR USE THEREOF

(71) Applicant: Temple University of the Commonwealth System of Higher Education, Philadelphia, PA (US)

(72) Inventors: Magid Abou-Gharbia, Exton, PA (US); Wayne E. Childers, New Hope, PA (US); Rogelio L. Martinez, Trenton, NJ (US); Mercy M. Ramanjulu, King of Prussia, PA (US); Benjamin E. Blass, Eagleville, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 18 days.

(21) Appl. No.: 14/895,681

(22) PCT Filed: Jun. 4, 2014

(86) PCT No.: PCT/US2014/040794
§ 371 (c)(1),
(2) Date: Dec. 3, 2015

(87) PCT Pub. No.: WO2014/197536
PCT Pub. Date: Dec. 11, 2014

(65) Prior Publication Data
US 2016/0229841 A1    Aug. 11, 2016

Related U.S. Application Data

(60) Provisional application No. 61/830,930, filed on Jun. 4, 2013.

(51) Int. Cl.
*C07D 403/06* (2006.01)
*C07D 471/08* (2006.01)
*C07D 487/08* (2006.01)
*C07D 205/08* (2006.01)

(52) U.S. Cl.
CPC ......... *C07D 403/06* (2013.01); *C07D 205/08* (2013.01); *C07D 471/08* (2013.01); *C07D 487/08* (2013.01)

(58) Field of Classification Search
CPC .. C07D 205/08; C07D 403/06; C07D 471/08; C07D 487/08
See application file for complete search history.

(56) References Cited

FOREIGN PATENT DOCUMENTS

| WO | 1999/067215 A1 | 12/1999 |
| WO | 2003/031407 A2 | 4/2003 |
| WO | 2005/077463 A2 | 8/2005 |
| WO | 2008/015269 A1 | 2/2008 |

OTHER PUBLICATIONS

Dresemann, G., "Imatinib and Hydroxyurea in pretreated progressive glioblastoma multiforme: a patient series", Annals of Oncology, 2005, 16, 1702-1708.
Azizi, S.A., et al., "Principles of treatment of malignant gliomas in adults: An overview", Journal of NeuroVirology, 1998, 4, 204-216.
Bossert, J.M. et al., "Neurobiology of relapse to heroin and cocaine seeking: An updated and clinical implications", European Journal of Pharmacology, 2005, 526, 36-50.
Chadwick, E.G. et al., "Single-dose ceftriaxone pharmacokinetics in pediatric patients with central nervous system infections", The Journal of Pediatrics, Jan. 1983, 102(1), 134-137.
de Groot, J. F. et al., "The Excitatory Amino Acid Transporter-2 Induces Apoptosis and Decreases Glioma Growth in vitro and in vivo", Cancer Research, Mar. 1, 2005, 65(5), 1934-1940.
Downey, K.K. et al., "Treatment of Heroin-Dependent Poly-Drug Abusers With Contingency Management and Buprenorphine Maintenance", Experimental and Clinical Psychopharmacology, 2000, 8(2), 176-184.
Dzubay, J. et al., "The Concentration of Synaptically Released Glutamate Outside of the Climbing Fiber-Purkinje Cell Synaptic Cleft", The Journal of Neuroscience, Jul. 1, 1999, 19(13), 5265-5274.
Goldstein, R.Z. et al., "Drug Addiction and its Underlying Neurobiological Basis: Neuroimaging Evidence for the Involvement of the Frontal Cortex", Am J Psychiatry, Oct. 2002, 159(10), 1642-1652.
Hartel, D.M. et al., "Heroin Use during Methadone Maintenance Treatment: The Importance of Methadone Dose and Cocaine Use", American Journal of Public Health, Jan. 1995, 85(1), 83-88.
Jemal, A. et al., "Cancer Statistics, 2006", CA a Cancer Journal for Clinicians, 2006, 56, 106-130.
Kalivas, P.W., "The glutamate homeostasis hypothesis of addiction", Nature Reviews/Neuroscience, Aug. 2009, 10, 561-572.
Kinsey, B.M. et al., "Anti-cocaine vaccine development", Expert Rev Vaccines, Sep. 2010, 9(9), 1109-1114.
Knackstedt, L.A. et al., "Ceftriaxone restores glutamate homeostasis and prevents relapse to cocaine-seeking", Biol Psychiatry, Jan. 2010, 67(1), 81-84.
Kreek, M.J. et al., "Opiate and Cocaine Addiction: From Bench to Clinic and Back to the Bench", Curr Opin Pharmacol, Feb. 2009, 9(1), 74-80.
Kreek, M.J. et al., "Drug dependence: stress and dysregulation of brain reward pathways", Drug and Alcohol Dependence, 1998, 51, 23-47.
Le Moal, M. et al., "Drug addiction: Pathways to the disease and pathophysiological perspectives", European Neuropsychopharmacology, 2007, 17, 377-393.
Lee, S-G. et al., "Mechanism of Ceftriaxone Induction of Excitatory Amino Acid Transporter-2 Expression and Glutamate Uptake in Primary Human Astrocytes", J Biol Chem, May 9, 2008, 283(19), 13116-13123.

(Continued)

*Primary Examiner* — Sreeni Padmanabhan
*Assistant Examiner* — Jody Karol
(74) *Attorney, Agent, or Firm* — Duane Morris LLP

(57) ABSTRACT

Pharmaceutical compositions of the invention comprise compounds, compositions, methods useful for the treatment of drug addiction, drug withdrawal, and diseases or conditions that involve dysregulation of glutamate homeostasis in it etiology.

9 Claims, 1 Drawing Sheet

(56) References Cited

OTHER PUBLICATIONS

Leri, F. et al., "Understanding polydrug use: review of heroin and cocaine co-use", Addiction, 2003, 98, 7-22.
Li, Y. et al., "Harmine, A Natural Beta-Carboline Alkaloid, Upregulates Astroglial Glutamate Transporter Expression", Neuropharmacology, Jun. 2011, 60(7-8), 1168-1175.
Lutsar, I. et al., "Pharmacokinetics and Pharmacodynamics of Cephalosporins in Cerebrospinal Fluid", Clin Pharmacokinet, Nov. 2000, 39(5), 335-343.
Magura, S. et al., "Pre- and in-treatment predictors of retention in methadone treatment using survival analysis", Addiction, 1998, 93(1), 51-60.
Maher, C.O., "Neurosurgical treatment of brain tumors in children", Pediatr Clin N Am, 2004, 51, 327-357.
Marcus, H.J. et al., "In vivo assessment of high-grade glioma biochemistry using microdailysis: a study of energy-related molecules, growth factors and cytokines", J Neurooncol, 2010, 97, 11-23.
Nakagawa, T. et al., "Effect of MS-153, a glutamate transporter activator, on the conditioned rewarding effects of morphine, methamphetamine and cocaine in mice", Behavioural Brain Research, 2005, 156, 233-239.
Piao, Y. et al., "AMPA receptors promote perivascular glioma invasion via Beta1 integrin-dependent adhesion to the extracellular matrix", Neuro-Oncology, Jun. 2009, 260-273.
Rawls, S. M. et al., "The Beta-lactam antibiotic ceftriaxone inhibits physical dependence and abstinence-inducted withdrawal form cocaine, amphetamine, methamphetamine, and clorazepate in planarians", European Journal of Pharmacology, 2008, 584, 278-284.
Reardon, D.A. et al., "Phase II Study of Imatinib Mesylate Plus Hydroxyurea in Adults with Recurrent Gliobastoma Multiforme", Jounral of Clinical Oncology, Dec. 20, 2005, 23(36), 9359-9368, Errata, p. 1224.
Reissner, K.J. et al., "Using glutamate homeostasis as a target for treating addictive disorders", Behav Pharmacol, Sep. 2010, 21(5-6), 514-522.
Roslin, M. et al., "Baseline levels of glucose metabolites, glutamate and glycerol in malignant glioma assessed by stereotactic microdialysis", Journal of Neuro-Oncology, 2003, 61, 151-160.
Rothstein, J.D. et al., "Beta-lactam antibiotics offer neuroprotection by increasing glutamate transporter expression", Nature, Jan. 6, 2005, 433, 73-77.
Sari, Y. et al., "Up-regulation of GLT1 attenuates cue-induced reinstatement of cocaine-seeking behaior in rats", J Neuroscience, Jul. 22, 2009, 29(29), 9239-9243.
Schmidt, H.D. et al., "Cocaine-induced neuroadaptations in glutamate transmission—Potential therapeutic targets for craving and addiction", Ann N.Y. Acad Sci, 2010, 1187, 35-75.
Shy, B. D. et al., "Limited Clinical Value of Bacterial Cocaine Esterase in Cocaine Toxicity", Annals of Emergency Medicine, May 2010, 55(5), 484-485.
Sontheimer, H., "A role for glutamate in growth and invasion of primary brain tumors", Journal of Neurochemistry, 2008, 105, 287-295.
Stotts, A.L., et al., "Using Acceptance and Commitment Therapy during Methadone Dose Reduction: Rationale, Treatment Description, and a Case Report", Cogn Behav Pract., May 1, 2009, 16(2), 205-213.
Tzschentke, T.M. et al., "Glutamatergic mechanisms in addiction", Molecular Psychiatry, 2003, 8, 373-382.
Uenishi, H. et al., "Ion Channel Modulation as the Basis for Neuroprotective Action of MS-153", Annals New York Academy of Sciences, 385-399.
van den Brink, W. et al., "Medical prescription of heroin to treatment resistant heroin addicts: two randomised controlled trials", BMJ, Aug. 9, 2003, 327, pp. 1-6.
Vanhoutte, N. et al., "Enhanced expression of the high affinity glutamate transporter GLT-1 in C6 glioma cells delays tumour progression in rat", Experimental Neurology, 2009, 218, 56-63.
Volkow, N.D. et al., "The Neural Basis of Addiction: A Pathology of Motivation and Choice", Am J Psychiatry, 2005, 162, 1403-1413.
Vorel, S.R. et al., "Dopamine D3 Receptor Antagonism Inhibits Cocaine-Seeking and Cocaine-Enhanced Brain Reward in Rats", The Journal of Neuroscience, Nov. 1, 2002, 22(21), 9595-9603.
Adamson, C. et al., "Glioblastoma multiforme: a review of where we have been and where we are going", Expert Opin. Investig. Drugs, 2009, 18(8), 1061-1083.
Huncharek, M. et al., "Treatment of Recurrent High Grade Astrocytoma; Results of a Systematic Review of 1,415 Patients", Anticancer Research, 1998, 18, 1303-1312.
International Search Report and Written Opinion issued for corresponding PCT Application No. PCT/US2014/040794, dated Sep. 8, 2016, 6 pages.
Extended European Search Report issued for corresponding European patent application No. 148078579.9, dated Jul. 21, 2017, 7 pages.

MC-100093 increase GLT-1 expression cocaine addiction model. Self-administration of cocaine in rats leads to decreased GLT-1 expression in rats. Treatment with MC-100093 (50mg/kg, IP, 6 days) restored GLT-1 expression levels to normal. * = $p<0.05$
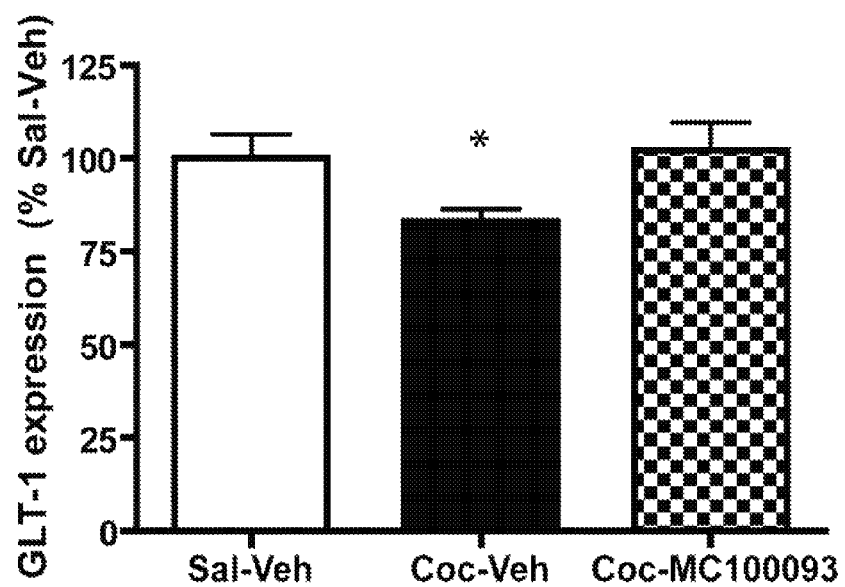

BETA LACTAMS AS MODULATORS OF GLUTAMATE UPTAKE AND METHODS FOR USE THEREOF

PRIORITY CLAIM AND CROSS-REFERENCE

This application claims the benefit of U.S. Provisional Application No. 61/830,930, filed Jun. 4, 2013, which application is expressly incorporated by reference herein in its entirety.

STATEMENT OF FEDERALLY FUNDED RESEARCH

The U.S. Government has a paid-up license in this invention and the right in limited circumstances to require the patent owner to license others on reasonable terms as provided for by the terms of grant number 5RC1DA028153-02 awarded by the National Institute on Drug Abuse.

FIELD OF THE INVENTION

The present disclosure relates to compositions and methods for the enhancement of glutamate uptake, useful in the treatment of drug addiction, drug withdrawal, related conditions and diseases that involve modulation of glutamate uptake in their etiology such as amyotrophic lateral sclerosis (ALS), malignant glioma, glioblastomas and glioblastoma multiforme (GBM).

BACKGROUND OF THE INVENTION

Illicit drug use continues to be a major public health concern in the United States. According to the US Department of Health and Human Services' 2009 National Survey on Drug Use and Health (US DDHS Report, 2009), an estimated 8.7% (21.8 million) of Americans age 12 or older reported being "current" illicit drug users, defined as having used a drug within one month of the survey. While the estimated number of American cocaine users age 12 or older has declined somewhat since 2006, it remains a major health concern, with approx. 16.7 million Americans (0.7% of the population) claiming to have used cocaine within a month of answering the survey. In addition, cocaine use is often seen as a complicating factor in cases of polyaddiction. There is a high prevalence of co-use of cocaine among heroin users (Leri et al., 2003). A high level of cocaine use has been shown to be an independent predictor of poor treatment outcome among heroin-dependent polydrug abusers (Downey et al., 2000). A degree of success in reducing heroin intake has been achieved through the use of opiate modulators such as methadone and buprenorphine (Stotts et al., 2009). However, studies suggest that the majority of cocaine/heroin abusers treated with methadone continued to use cocaine, even when the methadone reduced their heroin intake (Hartel et al., 1995; Magura et al., 1998). Thus, cocaine abuse represents a significant and complex health issue.

Addiction and recovery from addiction are characterized by a number of stages, each of which involves adaptations by various neurotransmitter systems (La Moel and Koob, 2007). In the early stages of the addiction process, the substance's ability to deliver reward plays a major role in drug use and continued use. As neuroadaptations take place over time, negative reinforcement augments the reward value of the drug, leading to dependence. Ultimately, when the drug is withdrawn after the establishment of dependence, a craving state occurs which can lead to relapse. Chronic exposure to cocaine induces marked alterations to the brain that make it difficult for many victims to withdraw from their use (Kreek and Koob, 1998; Bossert et al., 2005; Kreek et al., 2009). Dopaminergic signaling pathways play an important role in the reward learning and hedonic effects of cocaine abuse. However, several neurotransmitter systems may also be involved in addiction, including γ-aminobutyric acid (GABA), endocannabanoids, glutamate, endogenous opioids and serotonin (Goldstein and Volkow, 2002; Kalivas and Volkow, 2005). This complexity has made treatment of cocaine dependence a difficult goal to achieve. There are currently no FDA-approved medications for the treatment for cocaine addiction or withdrawal and there remains an urgent need for such medications (Van den Brink and van Ree, 2003; Kenna et al., 2007).

A number of marketed drugs and experimental agents targeting many of these neurotransmitter systems have recently entered clinical trials for the treatment of cocaine. Conventional efforts have targeted dopamine, serotonin, and norepinephrine systems. The strategy has resulted in the evaluation of at least 14 drugs as potential treatments (e.g. dopamine transporter inhibitors, L-DOPA, monoamine oxidase type B isozyme inhibitors, dopamine-releasing agents, dopamine D3 antagonists, 5-HT1A partial agonists, 5-HT reuptake inhibitors, etc.) (Vorel et al., 2002). Most of these agents produce adverse effects, including abuse liability, which limit their usefulness as abuse-deterrents. Other compounds being tested for cocaine addiction treatment are an anti-cocaine vaccine that retards entry of cocaine into the brain and a bacterial cocaine esterase that hydrolyzes cocaine into a nonpsychoactive metabolite (Ko et al., 2009; Kinsey et al., 2010). However, evidence that cocaine esterase has limited value in treating cocaine toxicity underscores the need to investigate alternative approaches (Shy et al., 2010).

Separately, Glioblastomas are malignant astrocytic tumors (WHO grade 4) and the most frequently occurring brain tumors. Disease prevalence is 1/100,000, and approximately 19,000 cases and 13,000 glioma related deaths are reported in the U.S. annually (Jemal, A., Siegel, R., Ward, E., Murray, T., Xu, J., Smigal, C. and Thun, M. J. *CA Cancer J. Clin.* 2006, 56, 106-130.) Glioblastomas can occur at any age, but 70% of cases occur in patients between 45 and 70. In addition, malignant gliomas are the most common solid cancer in children (Maher, C. O. and Raffel C. *Pediatr. Clin. North Am.* 2004, 51, 327-357). Survival time can be up to 5 years, but patients with glioblastoma multiforme (GBM), a deadly, invasive tumor, succumb to the disease within 6-12 months (Huncharek, M. and Muscat, J. *Anticancer Res.* 1998, 18, 1303-1311). The disease progresses rapidly (2-3 months) and symptoms resulting from intracranial hypertension are non-specific (headaches, vomiting, behavioral changes, neurological deficits), making diagnosis difficult. While there has been progress in developing new chemotherapeutic agents for many classes of cancer, there has been little progress towards the development of chemotherapeutic agents for malignant gliomas. Treatment options are limited, and often begin with surgery and biopsy to confirm diagnosis, but complete resection is rarely feasible, as tumor cells often infiltrate healthy brain tissue. Radiotherapy and chemotherapy can be employed, but the benefits from adjuvant treatments are modest as indicated by the minimal improvement in clinical outcomes using growth factor receptor antagonist treatments (EGFR, \PDGFR), mTOR inhibitors, AKT inhibitors, and PKC inhibitors ((a) Adamson C, Kanu O O, Mehta A I, Di C, Lin N, Mattox A K, Bigner D. D. *Expert Opin. Investig. Drugs* 2009, 18:1061-1083. (b) Dresemann G. *Ann Oncol* 2005; 16:1702-1708, Reardon, D. A., Egorin, M. J., Quinn, J. A., *J. Clin Oncol* 2005, 23, 9359-9368). Unfortunately, tumor incidence has increased over the past 30 years (Jemal, A., Siegel, R., Ward, E., Murray, T., Xu, J., Smigal, C. and Thun, M. J. *CA Cancer J. Clin.* 2006, 56, 106-130) and prognosis is poor in the majority of cases (Azizi S. A. and Miyamoto C. J. Neurovirol. 1998, 4, 204-216).

Separately, Amyotrophic lateral sclerosis (ALS) is a debilitating disease characterized by the death of both upper and lower motor neurons in the motor cortex of the brain, the brain stem, and the spinal cord. This leads to diminished motor function, muscle wasting, and death in 3-5 years. The lifetime risk of developing ALS is 1 in 1,000, and there are approximately 35,000 patients in the US with ALS. The financial burden of ALS is significant with late stage ventilation treatment typically lasting up to 2 years at a cost of up to $400K per year. To date, Riluzole is the only medication approved for the treatment of ALS. The current standard of care is 50 mg of Riluzole daily and palliative drugs to address disease symptoms. The clinical efficacy of this therapy is limited, however, as it increases life expectancy by only 2-3 months after 15 months of treatment.

It has been demonstrated that nearly 75% of ALS patients have significantly decreased GLT-1 levels, which contributes to the rapid decline of patients via glutamate toxicity and neuronal cell death. Modulation of GLT-1 expression levels in ALS patients is an attractive target for therapeutic intervention in ALS. The SOD1 mouse model of ALS is based upon the decreased expression of GLT-1 in this strain of mouse. It has been demonstrated that ceftriaxone, a beta-lactam antibiotic, increases the expression of GLT-1 in the SOD1 mouse model of ALS, and this increase in GLT-1 increases the mean survival time of the SOD1 mouse through increased expression of GLT-1 (Rothstein, J. D.; Patel, S.; Regan, M. R.; Haenggeli, C.; Huang, Y. H.; Bergles, D. E.; Jin, L.; Hoberg, M. D.; Vidensky, S.; Chung, D. S.; Toan, S. V.; Bruijn, L. I.; Su, Z. Z.; Gupta, P; Fisher, P. B. *Nature,* 2005, 433, 73-77). Harmine, a beta-carboline alkaloid, also increases GLT-1 expression in the SOD1 mouse model of ALS (Li, Y.; Sattler, R.; Yang, E. J.; Nunes, A.; Ayukawa, Y.; Akhtar, S.; Ji, G.; Zhang, P. W; Rothstein, J. R. *Neuropharmacology,* 2011, 60, 1168-1175). Neither of these compounds has been approved for clinical uses as a treatment for ALS, and to date there are no modulators of glutamate uptake available for clinical use as treatments for ALS.

SUMMARY OF THE INVENTION

The present invention is directed toward novel modulators of glutamate uptake, compounds of formula (I),

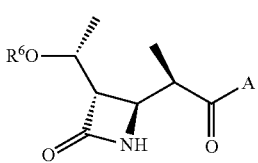

(I)

including hydrates, solvates, pharmaceutically acceptable salts, prodrugs and complexes thereof, wherein:

A is selected from the group consisting of

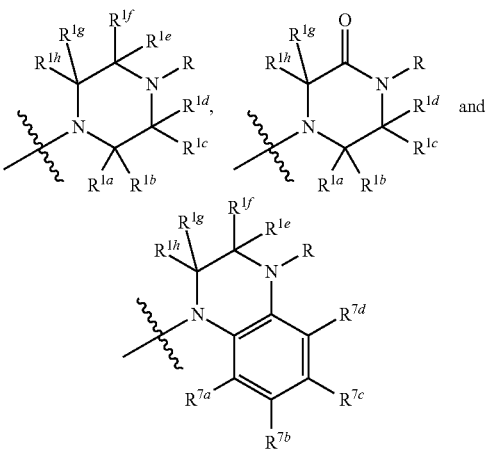

R is selected from the group consisting of hydrogen, $C_{1-6}$ linear alkyl, $C_{1-6}$ branched alkyl, optionally substituted aryl, $C(O)R^2$, $C(O)OR^3$, $C(O)NR^{4a}R^{4b}$, $SO_2R^5$, and $SO_2NH_2$;

$R^{1a}$, $R^{1b}$, $R^{1c}$, $R^{1d}$, $R^{1e}$, $R^{1f}$, $R^{1g}$, and $R^{1h}$ are each independently selected from the group consisting of hydrogen, $C_{1-6}$ linear alkyl, and $C_{1-6}$ branch alkyl;

In some embodiments, $R^{1b}$ and $R^{1g}$ are joined together with the atoms to which they are bound to form a ring containing 5, 6, or 7 atoms;

In some embodiments, $R^{1b}$ and $R^{1f}$ are joined together with the atoms to which they are bound to form a ring containing 5, 6, or 7 atoms;

In some embodiments, $R^{1d}$ and $R^{1f}$ are joined together with the atoms to which they are bound to form a ring containing 5, 6, or 7 atoms;

In some embodiments, $R^{1b}$ and $R^{1c}$ are joined together with the atoms to which they are bound to form a ring containing 5 or 6 atoms;

$R^2$ is selected from the group consisting of $C_{1-6}$ linear alkyl, $C_{1-6}$ branched alkyl, and optionally substituted aryl;

$R^3$ is selected from the group consisting of $C_{1-6}$ linear alkyl, $C_{1-6}$ branched alkyl, and optionally substituted aryl;

$R^{4a}$ is selected from the group consisting of $C_{1-6}$ linear alkyl, $C_{1-6}$ branched alkyl, and optionally substituted aryl;

$R^{4b}$ is selected from the group consisting of $C_{1-6}$ linear alkyl, $C_{1-6}$ branched alkyl, and optionally substituted aryl;

$R^5$ is selected from the group consisting of $C_{1-6}$ linear alkyl, $C_{1-6}$ branched alkyl, and optionally substituted aryl;

$R^6$ is selected from the group consisting of hydrogen, $C_{1-6}$ linear alkyl, and $C(O)R^8$;

$R^{7a}$, $R^{7b}$, $R^{7c}$, and $R^{7d}$ are each independently selected from the group consisting of are each independently selected from a group consisting of hydrogen, halogen, OH, $C_{1-6}$ linear alkyl, $C_{1-6}$ branched alkyl, $C_{1-6}$ alkoxy, $C_{1-6}$ haloalkyl, $C_{1-6}$ haloalkoxy, cyano, $NH(C_{1-6}$ alkyl), $N(C_{1-6}$ alkyl$)_2$, $NHC(O)R^8$, $C(O)NHR^8$, $C(O)N(R^8)_2$, SH, $SC_{1-6}$ alkyl, $SO_2NH_2$, $SO_2NHR^8$, $SO_2R^8$, and $NHSO_2R^8$;

$R^8$ is independently selected at each occurrence from a group consisting of hydrogen, $C_{1-6}$ linear alkyl, $C_{1-6}$ branched alkyl, and $C_{3-7}$ cycloalkyl;

The present invention further relates to compositions comprising:
an effective amount of one or more compounds according to the present invention and an excipient.

The present invention also relates to a method for treating drug addiction, drug withdrawal, related conditions, and diseases that involve dysregulation of glutamate homeostasis in their etiology, said method comprising administering to a subject an effective amount of a compound or composition according to the present invention.

The present invention yet further relates to a method for treating drug addiction, drug withdrawal, related conditions, and diseases that involve dysregulation of glutamate homeostasis in their etiology, wherein said method comprises administering to a subject a composition comprising an effective amount of one or more compounds according to the present invention and an excipient.

The present invention also relates to a method for treating or preventing disease or conditions associated with drug addiction, drug withdrawal, related conditions, and diseases that involve dysregulation of glutamate homeostasis in their etiology. Said methods comprise administering to a subject an effective amount of a compound or composition according to the present invention.

The present invention yet further relates to a method for treating or preventing disease or conditions associated with drug addiction, drug withdrawal, related conditions, and diseases that involve dysregulation of glutamate homeostasis in their etiology, wherein said method comprises administering to a subject a composition comprising an effective amount of one or more compounds according to the present invention and an excipient.

The present invention also relates to a method for treating or preventing disease or conditions associated with dysregulation of glutamate homeostasis. Said methods comprise administering to a subject an effective amount of a compound or composition according to the present invention.

The present invention yet further relates to a method for treating or preventing disease or conditions associated with dysregulation of glutamate homeostasis, wherein said method comprises administering to a subject a composition comprising an effective amount of one or more compounds according to the present invention and an excipient.

The present invention also relates to a method for treating amyotrophic lateral sclerosis, said method comprising administering to a subject an effective amount of a compound or composition according to the present invention.

The present invention yet further relates to a method for treating amyotrophic lateral sclerosis, wherein said method comprises administering to a subject a composition comprising an effective amount of one or more compounds according to the present invention and an excipient.

The present invention also relates to a method for treating malignant glioma, said method comprising administering to a subject an effective amount of a compound or composition according to the present invention.

The present invention yet further relates to a method for treating malignant glioma, wherein said method comprises administering to a subject a composition comprising an effective amount of one or more compounds according to the present invention and an excipient.

The present invention also relates to a method for treating glioblastomas, said method comprising administering to a subject an effective amount of a compound or composition according to the present invention.

The present invention yet further relates to a method for treating glioblastomas, wherein said method comprises administering to a subject a composition comprising an effective amount of one or more compounds according to the present invention and an excipient.

The present invention also relates to a method for treating glioblastoma multiforme, said method comprising administering to a subject an effective amount of a compound or composition according to the present invention.

The present invention yet further relates to a method for treating glioblastoma multiforme, wherein said method comprises administering to a subject a composition comprising an effective amount of one or more compounds according to the present invention and an excipient.

The present invention further relates to a process for preparing the compounds of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF THE DRAWING AND FIGURES

FIG. 1: MC-100093 increase GLT-1 expression cocaine addiction model. Self-administration of cocaine in rats leads to decreased GLT-1 expression in rats. Treatment with MC-100093 (50 mg/kg, IP, 6 days) restored GLT-1 expression levels to normal. *=p<0.05.

DETAILED DESCRIPTION OF THE INVENTION

There is a long felt need for new treatments of illicit drug addiction, drug withdrawal, and related conditions that are effective in treating patients for these conditions. There is also a long felt need for new treatments for diseases that involve modulation of glutamate uptake in their etiology such as amyotrophic lateral sclerosis (ALS), malignant glioma, glioblastomas and glioblastoma multiforme (GBM). The present invention addresses the need for new treatments of illicit drug addiction, drug withdrawal, and related conditions. The present invention also addresses the long felt need for new treatments for and means of preventing diseases that involve modulation of glutamate uptake in their etiology such as amyotrophic lateral sclerosis (ALS), malignant glioma, glioblastomas and glioblastoma multiforme (GBM). The beta lactams of the present invention are capable of treating drug addiction, withdrawal, related conditions and diseases that involve the modulation of glutamate uptake in their etiology such as amyotrophic lateral sclerosis (ALS), malignant glioma, glioblastomas and glioblastoma multiforme (GBM).

One neurotransmitter system that may have implications in addiction to multiple classes of illicit drugs is the glutamate system (Tzschentke and Wchmidt, 2003). Glutamate may be involved in many of the behaviors associated with addiction, and data suggest that dysregulation of glutamate homeostasis may play a significant role in the addiction process (Kalivas, 2009; Reissner and Kalivas, 2010). Chronic exposure to cocaine results in decreased levels of synaptic glutamate in the projections from the prefrontal cortex to the nucleus accumbens which, in turn, induces adaptive changes to the neurophysiology of the glutamatergic synapse (Schmidt and Pierce, 2010). The result of these changes is an impaired ability to regulate the increases in synaptic glutamate that occur in response to reinstatement of the drug, which may contribute to drug seeking and relapse. Among the changes that have been identified include down regulation of the cysteine-glutamate exchanger (xCT, the primary non-synaptic glutamate transporter) and GLT-1 (EAAT2, the primary synaptic glutamate transporter, located on astrocytes). It has been hypothesized that modulation of one or both of these transporter activities might stabilize cocaine-induced imbalance in glutamate homeostasis. Therefore, the cysteine-glutamate exchanger (xCT) and GLT-1 represent potential drug targets for treating cocaine craving and relapse.

Self-administration of cocaine by rats resulted in a reduction in both GLT-1 and cysteine-glutamate exchanger expression. Until 2005, little pharmacological evidence existed that correlated GLT-1 enhancement with beneficial effects on cocaine dependence. Nakagura et al. (2005) showed that MS-153, a glutamate transport activator, inhibited the conditioned place preference induced by cocaine. However, the relevance of that data is compromised by the finding that MS-153 can also modulate glutamate release through its indirect activity on voltage-gated calcium channels (Uneishi et al., 1999). A blinded screen of 1,040 FDA-approved drugs and nutritionals identified the β-lactam antibiotic ceftriaxone (CTX) as a stimulator of GLT-1 expression (Rothstein et al., 2005; Lee et al., 2008). Ceftriaxone inhibits abstinence withdrawal from cocaine in a planarian model (Rawls et al., 2008), prevents relapse to cocaine seeking in rats and restores GLT-1 and cysteine-glutamate exchanger levels that have been decreased by repeated cocaine administration (Sari et al., 2009; Knackstead et al., 2010).

The data with ceftriaxone suggests that a GLT-1 expression modulator could be useful for treating cocaine withdrawal. The data with ceftriaxone also suggests that a xCT expression modulator could be useful for treating cocaine withdrawal. However, ceftriaxone itself is not a suitable choice for this purpose. Ceftriaxone must be administered intravenously and a drug targeted at a chronic or sub-chronic indication such as cocaine withdrawal requires oral administration to enhance compliance. Further, because of its antimicrobial activity, chronic use of ceftriaxone presents a risk of inducing resistant strains of bacteria. Long term use of ceftriaxone can also result in debilitating side effects such as diarrhea, especially at the high doses required to achieve therapeutically meaningful CNS concentrations due to ceftriaxone's low brain bioavailability (free, unbound cerebrospinal fluid/plasma ratio=1% based on AUCs (Lutsar and Friedland, 2000) and 2-13% based on Cmax (Chadwick et al., 1983)). To date, there are no examples of orally bioavailable, CNS penetrant GLT-1 enhancer that are devoid of antibiotic activity and suitable for the chronic use required for the treatment of drug addiction, withdrawal, related conditions.

Separately, Glioblastomas are malignant astrocytic tumors (WHO grade 4) and the most frequently occurring brain tumors. The disease progresses rapidly (2-3 months) and symptoms resulting from intracranial hypertension are non-specific (headaches, vomiting, behavioral changes, neurological deficits), making diagnosis difficult. While there has been progress in developing new chemotherapeutic agents for many classes of cancer, there has been little progress towards the development of chemotherapeutic agents for malignant gliomas. Treatment options are limited, and often begin with surgery and biopsy to confirm diagnosis, but complete resection is rarely feasible, as tumor cells often infiltrate healthy brain tissue. Radiotherapy and chemotherapy can be employed, but the benefits from adjuvant treatments are modest as indicated by the minimal improvement in clinical outcomes using growth factor receptor antagonist treatments (EGFR, \PDGFR), mTOR inhibitors, AKT inhibitors, and PKC inhibitors ((a) Adamson C, Kanu O O, Mehta A I, Di C, Lin N, Mattox A K, Bigner D. D. *Expert Opin. Investig. Drugs* 2009, 18:1061-1083. (b) Dresemann G. *Ann Oncol* 2005; 16:1702-1708, Reardon, D. A., Egorin, M. J., Quinn, J. A., *J. Clin Oncol* 2005, 23, 9359-9368). Unfortunately, tumor incidence has increased over the past 30 years (Jemal, A., Siegel, R., Ward, E., Murray, T., Xu, J., Smigal, C. and Thun, M. J. *CA Cancer J. Clin.* 2006, 56, 106-130) and prognosis is poor in the majority of cases (Azizi S. A. and Miyamoto C. J. *Neurovirol.* 1998, 4, 204-216).

Dysregulation of Glu homeostasis may be responsible for GBM progression ((a) Sontheimer, H. *J. Neurochem.* 2008, 105, 287-295. (b) de Groot, J. F., Liu, T. J., Fuller, G., and Yung, W. K. A. *Cancer Res.* 2005, 65, 5, 1934-1940). Glu is the predominant excitatory amino acid neurotransmitter and GLT-1 is the dominant astroglial protein that inactivates synaptic Glu (Li, Y., Sattle, R., Eun Ju Yang, E. J., Nune, A., Ayukawa, Y., Sadia Akhtar, S., Grace Ji, G., Ping-Wu Zhang, P., Jeffrey D. Rothstein, J. D. *Neuropharmacology* 2011, 60, 1168-1175). It is released through $Ca^{2+}$ dependent fusion of synaptic vesicles from activated neurons. Once released, Glu binds to a number of receptors/transporter systems that mediate biological responses. While Glu levels are normally tightly controlled, this is not the case in GBM. Normal Glu brain levels do not exceed 1-3 µm (Dzubay J. A. and Jahr C. E. *J Neurosci* 1999, 19, 5265-5274), but studies of GBM patients using microdialysis probes to monitor brain Glu concentrations demonstrated Glu levels of >100 µM at tumor margins ((a) Marcus, H., Carpenter, K., Price, S. J., Hutchinson P. J. *J. Neurooncol.* 2010, 97, 11-23. (b) Roslin, M., Henriksson, R., Bergstrom, P., Ungerstedt, U., Bergenheim, A. T. *J. Neurooncol.* 2003, 61, 151-160). GLT-1 is the key transporter that normally removes >95% of synaptic Glu, but down regulation of its expression has been correlated with tumor grade, growth, and expansion (de Groot, J. F., Liu, T. J., Fuller, G., and Yung, W. K. A. *Cancer Res.* 2005, 65, 5, 1934-1940). In addition to GLT-1 down-regulation, glioma cells demonstrate increased expression levels of glutamate-cysteine exchanger system xc-, which increases glutamate release from glioma cells. The resulting high levels of Glu promote tumor growth and tissue invasion via excitotoxic cell death in the surrounding tissue creating space for tumor expansion within the restricted space of the cranial cavity (Sontheimer, H. *J. Neurochem.* 2008, 105, 287-295). Further, Glu has been implicated in abnormal cell signaling processes controlling cell motility and invasion through autocrine mechanisms wherein Glu secreted from glioma cells activates signaling pathways responsible for cellular proliferative processes (MAPK: random migration, Akt: survival, invasion, FAK: cell migration) (Piao Y, Lu L, de Groot J. *Neuro Oncol* 2009, 11:260-273). Interestingly, enhancing Glu transport by overexpressing GLT-1 in glioma cells in vitro and in vivo reduced cell proliferation and tumor growth in 2 independent studies ((a) de Groot, J. F., Liu, T. J., Fuller, G., and Yung, W. K. A. *Cancer Res.* 2005, 65, 5, 1934-1940. (b) Vanhoutte, N., Quinones, J. A., Jordan, B. F., Gallez, B., Maloteaux, J. M. and Hermans, E. *Experimental Neurology*, 2009, 218, 56-63), suggesting a significant role for GLT-1 in GBM. Specifically, de Groot et. al. transfected human glioblastoma cell lines U87, U373, SNB19, and U251 with a GLT-1 adenoviral vector in order to increase GLT-1 expression. A comparison of proliferation rates of Ad-GLT-1 cell lines with the standard gliobastoma cell lines demonstrated a clear time and expression level dependent decrease in cell proliferation. Further, subcutaneously implantation of Ad-GLT-1 U87 cells into nude mice were determined to be incapable of forming tumors, strongly suggesting that increased expression of GLT-1 leads to suppression of tumor formation (de Groot, J. F., Liu, T. J., Fuller, G., and Yung, W. K. A. *Cancer Res.* 2005, 65, 5, 1934-1940). To date, there are no GLT-1 expression modulators available for the treatment of malignant glioma, glioblastomas and glioblastoma multiforme (GBM).

Separately, Amyotrophic lateral sclerosis (ALS) is a debilitating disease characterized by the death of both upper and lower motor neurons in the motor cortex of the brain, the brain stem, and the spinal cord. This leads to diminished motor function, muscle wasting, and death in 3-5 years. To date, Riluzole is the only medication approved for the treatment of ALS. The current standard of care is 50 mg of Riluzole daily and palliative drugs to address disease symptoms. The clinical efficacy of this therapy is limited, however, as it increases life expectancy by only 2-3 months after 15 months of treatment.

It has been demonstrated that nearly 75% of ALS patients have significantly decreased GLT-1 levels, which contributes to the rapid decline of patients via glutamate toxicity and neuronal cell death. Modulation of GLT-1 expression levels in ALS patients is an attractive target for therapeutic intervention in ALS. The SOD1 mouse model of ALS is based upon the decreased expression of GLT-1 in this strain of mouse. It has been demonstrated that ceftriaxone, a beta-lactam antibiotic, increases the expression of GLT-1 in the SOD1 mouse model of ALS, and this increase in GLT-1 increases the mean survival time of the SOD1 mouse through increased expression of GLT-1 (Rothstein, J. D.; Patel, S.; Regan, M. R.; Haenggeli, C.; Huang, Y. H.; Bergles, D. E.; Jin, L.; Hoberg, M. D.; Vidensky, S.; Chung, D. S.; Toan, S. V.; Bruijn, L. I.; Su, Z. Z.; Gupta, P; Fisher, P. B. *Nature,* 2005, 433, 73-77). Harmine, a beta-carboline alkaloid, also increases GLT-1 expression in the SOD1 mouse model of ALS (Li, Y.; Sattler, R.; Yang, E. J.; Nunes, A.; Ayukawa, Y.; Akhtar, S.; Ji, G.; Zhang, P. W; Rothstein, J. R. *Neuropharmacology,* 2011, 60, 1168-1175). Neither of these compounds has been approved for clinical uses as a treatment for ALS, and to date there are no modulators of glutamate uptake available for clinical use as treatments for ALS.

There is a long felt need for new treatments of illicit drug addiction, drug withdrawal, and related conditions that are effective in treating patients for these conditions. There is also a long felt need for new treatments for diseases that involve modulation of glutamate uptake in their etiology such as amyotrophic lateral sclerosis (ALS), malignant glioma, glioblastomas and glioblastoma multiforme (GBM). The present invention addresses the need for new treatments of illicit drug addiction, drug withdrawal, and related conditions. The present invention also addresses the long felt need for new treatments for and means of preventing diseases that involve modulation of glutamate uptake in their etiology such as amyotrophic lateral sclerosis (ALS), malignant glioma, glioblastomas and glioblastoma multiforme (GBM).

It has been discovered that compounds of the disclosure are capable of enhancing glutamate uptake. Without wishing to be limited by theory, it is believed that the beta lactams of the present inventions can ameliorate, abate, otherwise cause to be controlled drug addiction, drug withdrawal, related conditions, and diseases that involve modulation of glutamate uptake in their etiology such as amyotrophic lateral sclerosis (ALS), malignant glioma, glioblastomas and glioblastoma multiforme (GBM).

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, $CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 1-phenyl-1-methylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted. Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

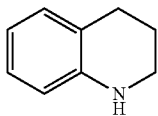

is, for the purposes of the present invention, considered a heterocyclic unit. 6,7-Dihydro-5H-cyclopentapyrimidine having the formula:

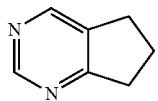

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

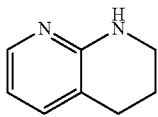

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^9$, —SR$^9$, —N(R$^9$)$_2$, —NR$^9$C(O)R$^9$, —SO$_2$R$^9$, —SO$_2$OR$^9$, —SO$_2$N(R$^9$)$_2$, —C(O)R$^9$, —C(O)OR$^9$, —C(O)N(R$^9$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^9$; wherein R$^9$, at each occurrence, independently is hydrogen, —OR$^{10}$, —SR$^{10}$, —C(O)R$^{10}$, —C(O)OR$^{10}$, —C(O)N(R$^{10}$)$_2$, —SO$_2$R$^{10}$, —S(O)$_2$OR$^{10}$, —N(R$^{10}$)$_2$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^x$ units taken together with the atom(s) to which they are bound form an optionally substituted carbocycle or heterocycle wherein said carbocycle or heterocycle has 3 to 7 ring atoms; wherein R$^{10}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{10}$ units taken together with the atom(s) to which they are bound form an optionally substituted carbocycle or heterocycle wherein said carbocycle or heterocycle preferably has 3 to 7 ring atoms.

In some embodiments, the substituents are selected from i) —OR$^{11}$; for example, —OH, —OCH$_3$, —OCH$_2$CH$_3$, —OCH$_2$CH$_2$CH$_3$;

ii) —C(O)R$^{11}$; for example, —COCH$_3$, —COCH$_2$CH$_3$, —COCH$_2$CH$_2$CH$_3$;

iii) —C(O)OR$^{11}$; for example, —CO$_2$CH$_3$, —CO$_2$CH$_2$CH$_3$, —CO$_2$CH$_2$CH$_2$CH$_3$;

iv) —C(O)N(R$^{11}$)$_2$; for example, —CONH$_2$, —CONHCH$_3$, —CON(CH$_3$)$_2$;

v) —N(R$^{11}$)$_2$; for example, —NH$_2$, —NHCH$_3$, —N(CH$_3$)$_2$, —NH(CH$_2$CH$_3$);

vi) halogen: —F, —Cl, —Br, —I, or combinations thereof;

vii) —CH$_e$X$_g$; wherein X is halogen, m is from 0 to 2, e+g=3; for example, —CH$_2$F, —CHF$_2$, —CF$_3$, —CCl$_3$, or —CBr$_3$;

viii) —SO$_2$R$^{11}$; for example, —SO$_2$H; —SO$_2$CH$_3$; —SO$_2$C$_6$H$_5$;

ix) $C_1$-$C_6$ linear, branched, or cyclic alkyl;

x) Cyano xi) Nitro;

xii) N(R$^{11}$)C(O)R$^{11}$;

xiii) Oxo (=O);

xiv) Heterocycle; and xv) Heteroaryl.

wherein each $R^{11}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g. optionally substituted $C_3$-$C_4$ cycloalkyl); or two $R^{11}$ units can be taken together to form a ring comprising 3-7 ring atoms. In certain aspects, each $R^{11}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the beta lactams described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^7)_2$, each $R^7$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The present invention is directed toward novel beta lactam derivatives, compounds of formula (I),

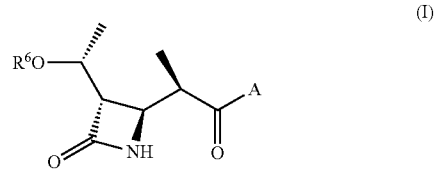

including hydrates, solvates, pharmaceutically acceptable salts, prodrugs and complexes thereof, wherein:
A is selected from the group consisting of

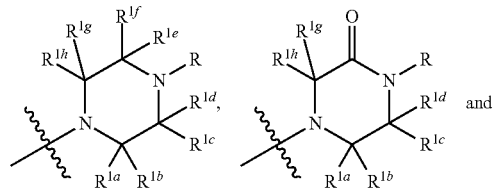

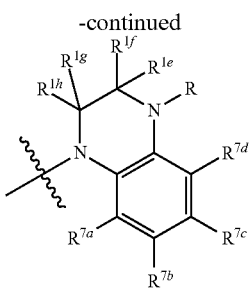

R is selected from the group consisting of hydrogen, $C_{1-6}$ linear alkyl, $C_{1-6}$ branched alkyl, optionally substituted aryl, $C(O)R^2$, $C(O)OR^3$, $C(O)NR^{4a}R^{4b}$, $SO_2R^5$, and $SO_2NH_2$;

$R^{1a}$, $R^{1b}$, $R^{1c}$, $R^{1d}$, $R^{1e}$, $R^{1f}$, $R^{1g}$, and $R^{1h}$ are each independently selected from the group consisting of hydrogen, $C_{1-6}$ linear alkyl, and $C_{1-6}$ branch alkyl;

In some embodiments, $R^{1b}$ and $R^{1g}$ are joined together with the atoms to which they are bound to form a ring containing 5, 6, or 7 atoms;

In some embodiments, $R^{1b}$ and $R^{1f}$ are joined together with the atoms to which they are bound to form a ring containing 5, 6, or 7 atoms;

In some embodiments, $R^{1d}$ and $R^{1f}$ are joined together with the atoms to which they are bound to form a ring containing 5, 6, or 7 atoms;

In some embodiments, $R^{1b}$ and $R^{1c}$ are joined together with the atoms to which they are bound to form a ring containing 5 or 6 atoms;

$R^2$ is selected from the group consisting of $C_{1-6}$ linear alkyl, $C_{1-6}$ branched alkyl, and optionally substituted aryl;

$R^3$ is selected from the group consisting of $C_{1-6}$ linear alkyl, $C_{1-6}$ branched alkyl, and optionally substituted aryl;

$R^{4a}$ is selected from the group consisting of $C_{1-6}$ linear alkyl, $C_{1-6}$ branched alkyl, and optionally substituted aryl;

$R^{4b}$ is selected from the group consisting of $C_{1-6}$ linear alkyl, $C_{1-6}$ branched alkyl, and optionally substituted aryl;

$R^5$ is selected from the group consisting of $C_{1-6}$ linear alkyl, $C_{1-6}$ branched alkyl, and optionally substituted aryl;

$R^6$ is selected from the group consisting of hydrogen, $C_{1-6}$ linear alkyl, and $C(O)R^8$:

$R^{7a}$, $R^{7b}$, $R^{7c}$, and $R^{7d}$ are each independently selected from the group consisting of are each independently selected from a group consisting of hydrogen, halogen, OH, $C_{1-6}$ linear alkyl, $C_{1-6}$ branched alkyl, $C_{1-6}$ alkoxy, $C_{1-6}$ haloalkyl, $C_{1-6}$ haloalkoxy, cyano, $NH(C_{1-6}$ alkyl), $N(C_{1-6}$ alkyl)$_2$, $NHC(O)R^8$, $C(O)NHR^8$, $C(O)N(R^8)_2$, SH, $SC_{1-6}$ alkyl, $SO_2NH_2$, $SO_2NHR^8$, $SO_2R^8$, and $NHSO_2R^8$;

$R^8$ is independently selected at each occurrence from a group consisting of hydrogen, $C_{1-6}$ linear alkyl, $C_{1-6}$ branched alkyl, and $C_{3-7}$ cycloalkyl;

In some embodiments A is

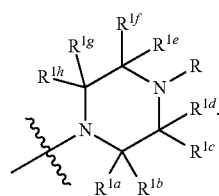

In some embodiments A is

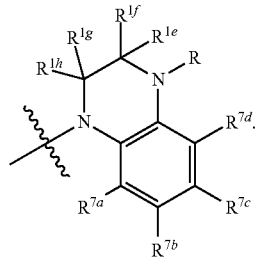

In some embodiments A is

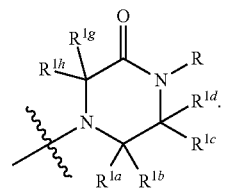

In some embodiments R is hydrogen.
In some embodiments R is $C_{1-6}$ linear alkyl.
In some embodiments R is $C_{1-6}$ branched alkyl.
In some embodiments R is optionally substituted aryl.
In some embodiments R is $C(O)R^2$.
In some embodiments R is $C(O)OR^3$.
In some embodiments R is $C(O)NR^{4a}R^{4b}$.
In some embodiments R is $SO_2R^5$.
In some embodiments R is $SO_2NH_2$.
In some embodiments $R^{1a}$ is hydrogen.
In some embodiments $R^{1a}$ is $C_{1-6}$ linear alkyl.
In some embodiments $R^{1a}$ is $C_{1-6}$ branch alkyl.
In some embodiments $R^{1b}$ is hydrogen.
In some embodiments $R^{1b}$ is $C_{1-6}$ linear alkyl.
In some embodiments $R^{1b}$ is $C_{1-6}$ branch alkyl.
In some embodiments $R^{1c}$ is hydrogen.
In some embodiments $R^{1c}$ is $C_{1-6}$ linear alkyl.
In some embodiments $R^{1c}$ is $C_{1-6}$ branch alkyl.
In some embodiments $R^{1d}$ is hydrogen.
In some embodiments $R^{1d}$ is $C_{1-6}$ linear alkyl.
In some embodiments $R^{1d}$ is $C_{1-6}$ branch alkyl.
In some embodiments $R^{1e}$ is hydrogen.
In some embodiments $R^{1e}$ is $C_{1-6}$ linear alkyl.
In some embodiments $R^{1e}$ is $C_{1-6}$ branch alkyl.
In some embodiments $R^{1f}$ is hydrogen.
In some embodiments $R^{1f}$ is $C_{1-6}$ linear alkyl.
In some embodiments $R^{1f}$ is $C_{1-6}$ branch alkyl.
In some embodiments $R^{1g}$ is hydrogen.
In some embodiments $R^{1g}$ is $C_{1-6}$ linear alkyl.
In some embodiments $R^{1g}$ is $C_{1-6}$ branch alkyl.
In some embodiments $R^{1h}$ is hydrogen.
In some embodiments $R^{1h}$ is $C_{1-6}$ linear alkyl.
In some embodiments $R^{1h}$ is $C_{1-6}$ branch alkyl.
In some embodiments $R^{1b}$ and $R^{1g}$ are joined together with the atoms to which they are bound to form a ring containing 5 atoms.
In some embodiments $R^{1b}$ and $R^{1g}$ are joined together with the atoms to which they are bound to form a ring containing 6 atoms.
In some embodiments $R^{1b}$ and $R^{1g}$ are joined together with the atoms to which they are bound to form a ring containing 7 atoms.

In some embodiments $R^{1b}$ and $R^{1f}$ are joined together with the atoms to which they are bound to form a ring containing 5 atoms.

In some embodiments $R^{1b}$ and $R^{1f}$ are joined together with the atoms to which they are bound to form a ring containing 6 atoms.

In some embodiments $R^{1b}$ and $R^{1f}$ are joined together with the atoms to which they are bound to form a ring containing 7 atoms.

In some embodiments $R^{1d}$ and $R^{1f}$ are joined together with the atoms to which they are bound to form a ring containing 5 atoms In some embodiments $R^{1d}$ and $R^{1f}$ are joined together with the atoms to which they are bound to form a ring containing 6 atoms.

In some embodiments $R^{1d}$ and $R^{1f}$ are joined together with the atoms to which they are bound to form a ring containing 7 atoms.

In some embodiments $R^{1b}$ and $R^{1c}$ are joined together with the atoms to which they are bound to form a ring containing 5 atoms.

In some embodiments $R^{1b}$ and $R^{1c}$ are joined together with the atoms to which they are bound to form a ring containing 6 atoms.

In some embodiments $R^2$ is $C_{1-6}$ linear alkyl.
In some embodiments $R^2$ is $C_{1-6}$ branched alkyl.
In some embodiments $R^2$ is optionally substituted aryl.
In some embodiments $R^3$ is $C_{1-6}$ linear alkyl.
In some embodiments $R^3$ is $C_{1-6}$ branched alkyl.
In some embodiments $R^3$ is optionally substituted aryl.
In some embodiments $R^{4a}$ is $C_{1-6}$ linear alkyl.
In some embodiments $R^{4a}$ is $C_{1-6}$ branched alkyl.
In some embodiments $R^{4a}$ is optionally substituted aryl.
In some embodiments $R^{4b}$ is $C_{1-6}$ linear alkyl.
In some embodiments $R^{4b}$ is $C_{1-6}$ branched alkyl.
In some embodiments $R^{4b}$ is optionally substituted aryl.
In some embodiments $R^5$ is $C_{1-6}$ linear alkyl.
In some embodiments $R^5$ is $C_{1-6}$ branched alkyl.
In some embodiments $R^5$ is optionally substituted aryl.
In some embodiments $R^6$ is hydrogen.
In some embodiments $R^6$ is $C_{1-6}$ linear alkyl.
In some embodiments $R^6$ is $C(O)R^8$.
In some embodiments $R^{7a}$ is hydrogen.
In some embodiments $R^{7a}$ is halogen.
In some embodiments $R^{7a}$ is OH.
In some embodiments $R^{7a}$ is $C_{1-6}$ linear alkyl.
In some embodiments $R^{7a}$ is $C_{1-6}$ branched alkyl.
In some embodiments $R^{7a}$ is $C_{1-6}$ alkoxy.
In some embodiments $R^{7a}$ is $C_{1-6}$ haloalkyl.
In some embodiments $R^{7a}$ is $C_{1-6}$ haloalkoxy.
In some embodiments $R^{7a}$ is cyano.
In some embodiments $R^{7a}$ is $NH(C_{1-6}$ alkyl).
In some embodiments $R^{7a}$ is $N(C_{1-6}$ alkyl$)_2$.
In some embodiments $R^{7a}$ is $NHC(O)R^8$.
In some embodiments $R^{7a}$ is $C(O)NHR^8$.
In some embodiments $R^{7a}$ is $C(O)N(R^8)_2$.
In some embodiments $R^{7a}$ is SH.
In some embodiments $R^{7a}$ is $SC_{1-6}$ alkyl.
In some embodiments $R^{7a}$ is $SO_2NH_2$.
In some embodiments $R^{7a}$ is $SO_2NHR^8$.
In some embodiments $R^{7a}$ is $SO_2R^8$.
In some embodiments $R^{7a}$ is $NHSO_2R^8$.
In some embodiments $R^{7b}$ is hydrogen.
In some embodiments $R^{7b}$ is halogen.
In some embodiments $R^{7b}$ is OH.
In some embodiments $R^{7b}$ is $C_{1-6}$ linear alkyl.
In some embodiments $R^{7b}$ is $C_{1-6}$ branched alkyl.
In some embodiments $R^{7b}$ is $C_{1-6}$ alkoxy.
In some embodiments $R^{7b}$ is $C_{1-6}$ haloalkyl.
In some embodiments $R^{7b}$ is $C_{1-6}$ haloalkoxy.
In some embodiments $R^{7b}$ is cyano.
In some embodiments $R^{7b}$ is $NH(C_{1-6}$ alkyl).
In some embodiments $R^{7b}$ is $N(C_{1-6}$ alkyl$)_2$.
In some embodiments $R^{7b}$ is $NHC(O)R^8$.
In some embodiments $R^{7b}$ is $C(O)NHR^8$.
In some embodiments $R^{7b}$ is $C(O)N(R^8)_2$.
In some embodiments $R^{7b}$ is SH.
In some embodiments $R^{7b}$ is $SC_{1-6}$ alkyl.
In some embodiments $R^{7b}$ is $SO_2NH_2$.
In some embodiments $R^{7b}$ is $SO_2NHR^8$.
In some embodiments $R^{7b}$ is $SO_2R^8$.
In some embodiments $R^{7b}$ is $NHSO_2R^8$.
In some embodiments $R^{7c}$ is hydrogen.
In some embodiments $R^{7c}$ is halogen.
In some embodiments $R^{7c}$ is OH.
In some embodiments $R^{7c}$ is $C_{1-6}$ linear alkyl.
In some embodiments $R^{7c}$ is $C_{1-6}$ branched alkyl.
In some embodiments $R^{7c}$ is $C_{1-6}$ alkoxy.
In some embodiments $R^{7c}$ is $C_{1-6}$ haloalkyl.
In some embodiments $R^{7c}$ is $C_{1-6}$ haloalkoxy.
In some embodiments $R^{7c}$ is cyano.
In some embodiments $R^{7c}$ is $NH(C_{1-6}$ alkyl).
In some embodiments $R^{7c}$ is $N(C_{1-6}$ alkyl$)_2$.
In some embodiments $R^{7c}$ is $NHC(O)R^8$.
In some embodiments $R^{7c}$ is $C(O)NHR^8$.
In some embodiments $R^{7c}$ is $C(O)N(R^8)_2$.
In some embodiments $R^{7c}$ is SH.
In some embodiments $R^{7c}$ is $SC_{1-6}$ alkyl.
In some embodiments $R^{7c}$ is $SO_2NH_2$.
In some embodiments $R^{7c}$ is $SO_2NHR^8$.
In some embodiments $R^{7c}$ is $SO_2R^8$.
In some embodiments $R^{7c}$ is $NHSO_2R^8$.
In some embodiments $R^{7d}$ is hydrogen.
In some embodiments $R^{7d}$ is halogen.
In some embodiments $R^{7d}$ is OH.
In some embodiments $R^{7d}$ is $C_{1-6}$ linear alkyl.
In some embodiments $R^{7d}$ is $C_{1-6}$ branched alkyl.
In some embodiments $R^{7d}$ is $C_{1-6}$ alkoxy.
In some embodiments $R^{7d}$ is $C_{1-6}$ haloalkyl.
In some embodiments $R^{7d}$ is $C_{1-6}$ haloalkoxy.
In some embodiments $R^{7d}$ is cyano.
In some embodiments $R^{7d}$ is $NH(C_{1-6}$ alkyl).
In some embodiments $R^{7d}$ is $N(C_{1-6}$ alkyl$)_2$.
In some embodiments $R^{7d}$ is $NHC(O)R^8$.
In some embodiments $R^{7d}$ is $C(O)NHR^8$.
In some embodiments $R^{7d}$ is $C(O)N(R^8)_2$.
In some embodiments $R^{7d}$ is SH.
In some embodiments $R^{7d}$ is $SC_{1-6}$ alkyl.
In some embodiments $R^{7d}$ is $SO_2NH_2$.
In some embodiments $R^{7d}$ is $SO_2NHR^8$.
In some embodiments $R^{7d}$ is $SO_2R^8$.
In some embodiments $R^{7d}$ is $NHSO_2R^8$.
In some embodiments $R^8$ is hydrogen.
In some embodiments $R^8$ is $C_{1-6}$ linear alkyl.
In some embodiments $R^8$ is $C_{1-6}$ branched alkyl.
In some embodiments $R^8$ is $C_{3-7}$ cycloalkyl.

Exemplary embodiments include compounds having the formula (I) or a pharmaceutically acceptable salt form thereof:

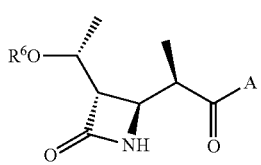

(I)

wherein non-limiting examples of $R^6$ and A are defined herein below in Table 1.

| Entry | $R^6$ | A |
|---|---|---|
| 1 | H | *N-piperazine-N-methyl* |
| 2 | H | *N-piperazine-N-t-butyl* |
| 3 | H | *N-(2,2,6,6-tetramethylpiperazine)-N-methyl* |
| 4 | H | *N-piperazine-N-phenyl* |
| 5 | H | *3,8-diazabicyclo[3.2.1] N-methyl* |
| 6 | H | *2,5-diazabicyclo[2.2.1] N-methyl* |
| 7 | $CH_3$ | *N-piperazine-N-methyl* |
| 8 | $CH_3$ | *N-piperazine-N-t-butyl* |
| 9 | $CH_3$ | *N-(2,2,6,6-tetramethylpiperazine)-N-methyl* |
| 10 | $CH_3$ | *N-piperazine-N-phenyl* |
| 11 | $CH_3$ | *3,8-diazabicyclo[3.2.1] N-methyl* |
| 12 | $CH_3$ | *2,5-diazabicyclo[2.2.1] N-methyl* |
| 13 | $CH_3C(=O)$ | *N-piperazine-N-methyl* |
| 14 | $CH_3C(=O)$ | *N-piperazine-N-t-butyl* |
| 15 | $CH_3C(=O)$ | *N-(2,2,6,6-tetramethylpiperazine)-N-methyl* |
| 16 | $CH_3C(=O)$ | *N-piperazine-N-phenyl* |
| 17 | $CH_3C(=O)$ | *3,8-diazabicyclo[3.2.1] N-methyl* |
| 18 | $CH_3C(=O)$ | *2,5-diazabicyclo[2.2.1] N-methyl* |
| 19 | H | *N-piperazine-N-Boc* |
| 20 | H | *N-piperazine-N-ethyl* |
| 21 | H | *N-piperazine-N-cyclohexyl* |
| 22 | H | *N-piperazine-N-phenyl* |
| 23 | $(CH_3)_2CHC(=O)$ | *N-piperazine-N-methyl* |
| 24 | $CH_3CH_2C(=O)$ | *N-piperazine-N-methyl* |

| Entry | R⁶ | A |
|---|---|---|
| 25 | CH₃(CH₂)₂C(=O) | N-methylpiperazinyl |
| 26 | H | 3,8-diazabicyclo[3.2.1] N-methyl |
| 27 | H | 4-acetylpiperazinyl |
| 28 | H | 4-carbamoylpiperazinyl |
| 29 | H | 4-(methylsulfonyl)piperazinyl |
| 30 | H | 4-methyl-3-oxopiperazinyl |
| 31 | H | 4-methyl-3,4-dihydroquinoxalin-1(2H)-yl |
| 32 | CH₃ | 3,8-diazabicyclo[3.2.1] N-methyl |
| 33 | CH₃ | 4-acetylpiperazinyl |
| 34 | CH₃ | 4-carbamoylpiperazinyl |
| 35 | CH₃ | 4-(methylsulfonyl)piperazinyl |
| 36 | CH₃ | 4-methyl-3-oxopiperazinyl |
| 37 | CH₃ | 4-methyl-3,4-dihydroquinoxalin-1(2H)-yl |
| 38 | CH₃C(=O) | 3,8-diazabicyclo[3.2.1] N-methyl |
| 39 | CH₃C(=O) | 4-acetylpiperazinyl |
| 40 | CH₃C(=O) | 4-carbamoylpiperazinyl |
| 41 | CH₃C(=O) | 4-(methylsulfonyl)piperazinyl |
| 42 | CH₃C(=O) | 4-methyl-3-oxopiperazinyl |
| 43 | CH₃C(=O) | 4-methyl-3,4-dihydroquinoxalin-1(2H)-yl |
| 44 | H | piperazinyl (NH) |
| 45 | (CH₃)₃C(=O) | N-methylpiperazinyl |
| 46 | H | 4-benzoylpiperazinyl |
| 47 | H | 4-propylpiperazinyl |
| 48 | H | 4-(4-methoxyphenyl)piperazinyl |

For the purposes of demonstrating the manner in which the compounds of the present invention are named and referred to herein, the compound having the formula:

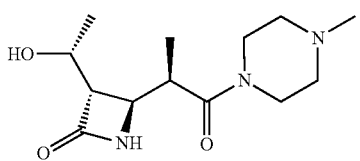 [SMILES: C[C@@H](O)[C@H]1C(=O)N[C@@H]1[C@@H](C)C(=O)N1CCN(C)CC1]

has the chemical name (3S,4R)-3-((R)-1-hydroxyethyl)-4-((R)-1-(4-methylpiperazin-1-yl)-1-oxopropan-2-yl)azetidin-2-one.

For the purposes of the present invention, a compound depicted by the racemic formula, for example:

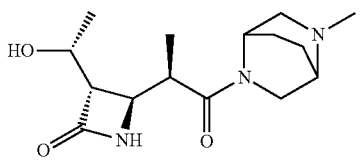 [SMILES: C[C@@H](O)[C@H]1C(=O)N[C@@H]1[C@@H](C)C(=O)N1CC2CCC1CN2C]

will stand equally well for either of the two enantiomers having the formula:

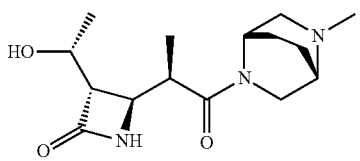 [SMILES: C[C@@H](O)[C@H]1C(=O)N[C@@H]1[C@@H](C)C(=O)N1C[C@@H]2CC[C@H]1CN2C]

or the formula:

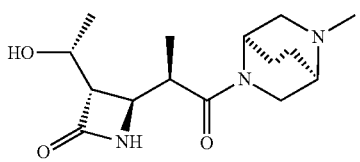

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the beta lactams of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds.

The reagents used in the preparation of the compounds of this invention can be either commercially obtained or can be prepared by standard procedures described in the literature. In accordance with this invention, compounds in the genus may be produced by one of the following reaction schemes.

Compounds of formula (4) may be prepared according to the process outlined in Scheme 1.

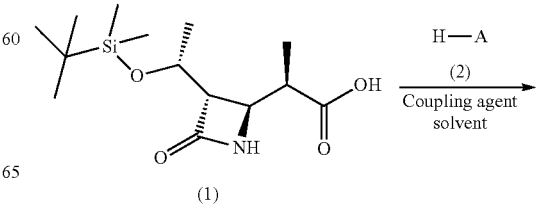

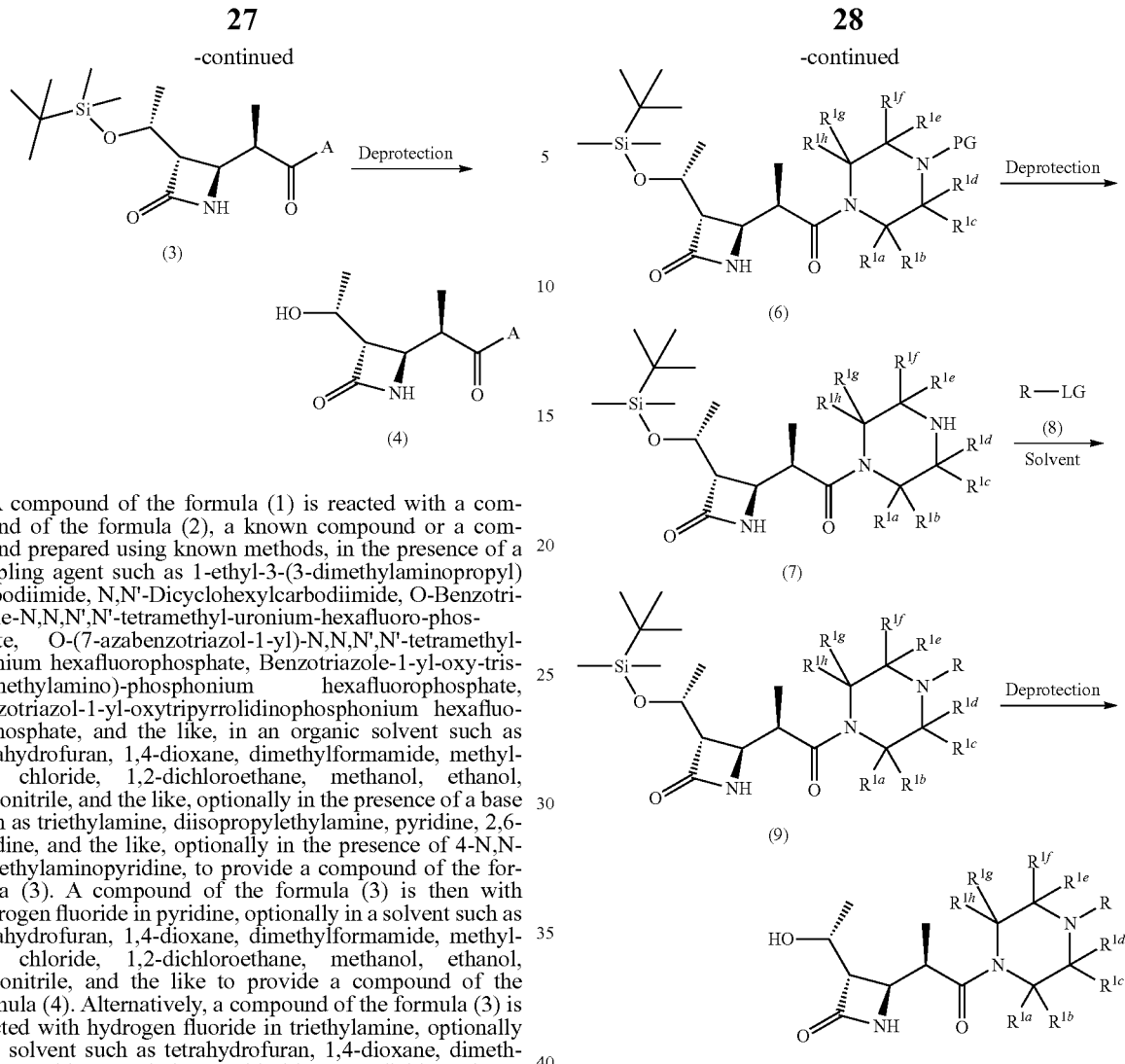

A compound of the formula (1) is reacted with a compound of the formula (2), a known compound or a compound prepared using known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, 1,2-dichloroethane, methanol, ethanol, acetonitrile, and the like, optionally in the presence of a base such as triethylamine, diisopropylethylamine, pyridine, 2,6-lutidine, and the like, optionally in the presence of 4-N,N-dimethylaminopyridine, to provide a compound of the formula (3). A compound of the formula (3) is then with hydrogen fluoride in pyridine, optionally in a solvent such as tetrahydrofuran, 1,4-dioxane, dimethylformamide, methylene chloride, 1,2-dichloroethane, methanol, ethanol, acetonitrile, and the like to provide a compound of the formula (4). Alternatively, a compound of the formula (3) is reacted with hydrogen fluoride in triethylamine, optionally in a solvent such as tetrahydrofuran, 1,4-dioxane, dimethylformamide, methylene chloride, 1,2-dichloroethane, methanol, ethanol, acetonitrile, and the like to provide a compound of the formula (4). Alternatively, a compound of the formula (3) is reacted with an acid such as hydrochloric acid, sulfuric acid, trifluoroacetic acid, acetic acid, and the like, optionally in a solvent such as tetrahydrofuran, 1,4-dioxane, dimethylformamide, methylene chloride, 1,2-dichloroethane, methanol, ethanol, acetonitrile, and the like to provide a compound of the formula (4).

Compounds of formula (10) may be prepared according to the process outlined in Scheme 2.

Scheme 2

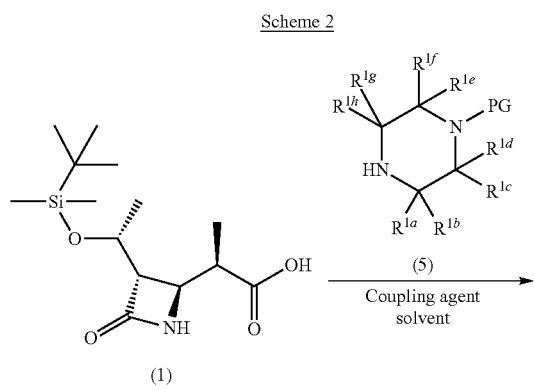

A compound of the formula (1) is reacted with a compound of the formula (5), a known compound or a compound prepared using known methods, wherein PG is a protecting group such as t-butyl carbamate, benzyl carbamate, 9-fluorenylmethyl carbamate, and the like, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, 1,2-dichloroethane, methanol, ethanol, acetonitrile, and the like, optionally in the presence of a base such as triethylamine, diisopropylethylamine, pyridine, 2,6-lutidine, and the like, optionally in the presence of 4-N,N-dimethylaminopyridine, to provide a compound of the formula (6). A compound of the formula (6) is then reacted with an acid such as hydrochloric acid, sulfuric acid, trifluoroacetic acid, acetic acid, and the like, optionally in a solvent such as tetrahydrofuran, 1,4-dioxane, dimethylformamide, methylene chloride, 1,2-dichloroethane, methanol, ethanol, acetonitrile, and the like to provide a compound of the formula (7). Alternatively, a compound of the formula (6) is reacted with hydrogen in the presence of a palladium catalyst such as palladium on carbon, palladium acetate, palladium bis(triphenylphosphine) dichloride, palladium tetrakis(triphenylphosphine), bis(acetonitrile), and the like, in an organic solvent such as methanol, ethanol, isopropanol, ethyl acetate, tetrahydrofuran, 1,4-dioxane, and the like to provide a compound of the formula (7). Alternatively, a compound of the formula (6) is reacted with a base such as piperidine, pyridine, triethylamine, and the like, optionally in the presence of a solvent such as tetrahydrofuran, 1,4-dioxane, dimethylformamide, methylene chloride, 1,2-dichloroethane, methanol, ethanol, acetonitrile, and the like to provide a compound of the formula (7). A compound of the formula (7) is then reacted with a compound of the formula (8), a known compound or a compound prepared by known means, wherein LG is a leaving group such as chloride, bromide, methanesulfonate, tosylate, and the like, in the presence of a base such as triethylamine, diisopropylethylamine, pyridine, and the like, in the presence of a solvent such as tetrahydrofuran, 1,4-dioxane, dimethylformamide, methylene chloride, 1,2-dichloroethane, methanol, ethanol, acetonitrile, and the like to provide a compound of the formula (9). A compound of the formula (9) is then with hydrogen fluoride in pyridine, optionally in a solvent such as tetrahydrofuran, 1,4-dioxane, dimethylformamide, methylene chloride, 1,2-dichloroethane, methanol, ethanol, acetonitrile, and the like to provide a compound of the formula (10). Alternatively, a compound of the formula (9) is reacted with hydrogen fluoride in triethylamine, optionally in a solvent such as tetrahydrofuran, 1,4-dioxane, dimethylformamide, methylene chloride, 1,2-dichloroethane, methanol, ethanol, acetonitrile, and the like to provide a compound of the formula (10). Alternatively, a compound of the formula (9) is reacted with an acid such as hydrochloric acid, sulfuric acid, trifluoroacetic acid, acetic acid, and the like, optionally in a solvent such as tetrahydrofuran, 1,4-dioxane, dimethylformamide, methylene chloride, 1,2-dichloroethane, methanol, ethanol, acetonitrile, and the like to provide a compound of the formula (10).

Compounds of formula (13) may be prepared according to the process outlined in Scheme 3.

Scheme 3

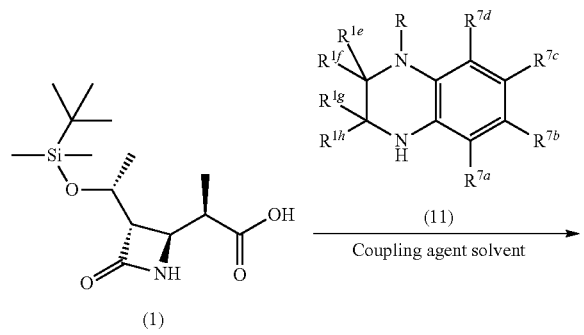

(1)

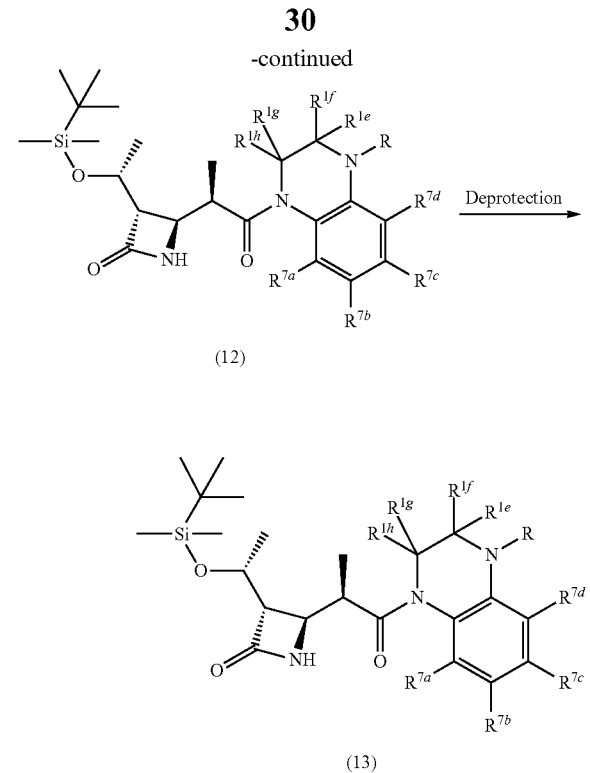

A compound of the formula (1) is reacted with a compound of the formula (11), a known compound or a compound prepared using known methods, in the presence of a coupling agent such as 1-ethyl-3-(3-dimethylaminopropyl) carbodiimide, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, in an organic solvent such as tetrahydrofuran, 1,4-dioxane, dimethylformamide, methylene chloride, 1,2-dichloroethane, methanol, ethanol, acetonitrile, and the like, optionally in the presence of a base such as triethylamine, diisopropylethylamine, pyridine, 2,6-lutidine, and the like, optionally in the presence of 4-N,N-dimethylaminopyridine, to provide a compound of the formula (12). A compound of the formula (12) is then with hydrogen fluoride in pyridine, optionally in a solvent such as tetrahydrofuran, 1,4-dioxane, dimethylformamide, methylene chloride, 1,2-dichloroethane, methanol, ethanol, acetonitrile, and the like to provide a compound of the formula (13). Alternatively, a compound of the formula (12) is reacted with hydrogen fluoride in triethylamine, optionally in a solvent such as tetrahydrofuran, 1,4-dioxane, dimethylformamide, methylene chloride, 1,2-dichloroethane, methanol, ethanol, acetonitrile, and the like to provide a compound of the formula (13). Alternatively, a compound of the formula (12) is reacted with an acid such as hydrochloric acid, sulfuric acid, trifluoroacetic acid, acetic acid, and the like, optionally in a solvent such as tetrahydrofuran, 1,4-dioxane, dimethylformamide, methylene chloride, 1,2-dichloroethane, methanol, ethanol, acetonitrile, and the like to provide a compound of the formula (13).

Compounds of formula (19) may be prepared according to the process outlined in Scheme 4.

Scheme 4

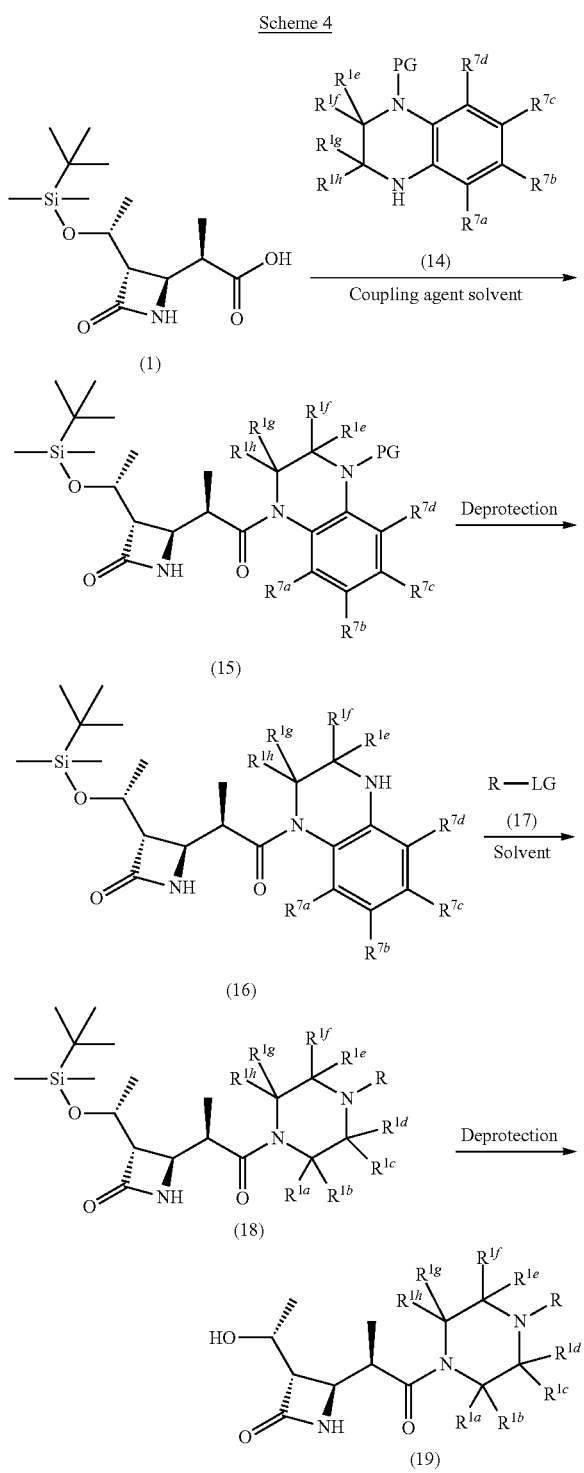

A compound of the formula (1) is reacted with a compound of the formula (14), a known compound or a compound prepared using known methods, wherein PG is a protecting group such as t-butyl carbamate, benzyl carbamate, 9-fluorenylmethyl carbamate, and the like, in the presence of a coupling agent such as 1-ethyl-3-(3-dimethylaminopropyl)carbodiimide, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, 1,2-dichloroethane, methanol, ethanol, acetonitrile, and the like, optionally in the presence of a base such as triethylamine, diisopropylethylamine, pyridine, 2,6-lutidine, and the like, optionally in the presence of 4-N,N-dimethylaminopyridine, to provide a compound of the formula (15). A compound of the formula (15) is then reacted with an acid such as hydrochloric acid, sulfuric acid, trifluoroacetic acid, acetic acid, and the like, optionally in a solvent such as tetrahydrofuran, 1,4-dioxane, dimethylformamide, methylene chloride, 1,2-dichloroethane, methanol, ethanol, acetonitrile, and the like to provide a compound of the formula (16). Alternatively, a compound of the formula (15) is reacted with hydrogen in the presence of a palladium catalyst such as palladium on carbon, palladium acetate, palladium bis(triphenylphosphine) dichloride, palladium tetrakis(triphenylphosphine), bis(acetonitrile), and the like, in an organic solvent such as methanol, ethanol, isopropanol, ethyl acetate, tetrahydrofuran, 1,4-dioxane, and the like to provide a compound of the formula (16). Alternatively, a compound of the formula (15) is reacted with a base such as piperidine, pyridine, triethylamine, and the like, optionally in the presence of a solvent such as tetrahydrofuran, 1,4-dioxane, dimethylformamide, methylene chloride, 1,2-dichloroethane, methanol, ethanol, acetonitrile, and the like to provide a compound of the formula (16). A compound of the formula (16) is then reacted with a compound of the formula (17), a known compound or a compound prepared by known means, wherein LG is a leaving group such as chloride, bromide, methanesulfonate, tosylate, and the like, in the presence of a base such as triethylamine, diisopropylethylamine, pyridine, and the like, in the presence of a solvent such as tetrahydrofuran, 1,4-dioxane, dimethylformamide, methylene chloride, 1,2-dichloroethane, methanol, ethanol, acetonitrile, and the like to provide a compound of the formula (18). A compound of the formula (18) is then with hydrogen fluoride in pyridine, optionally in a solvent such as tetrahydrofuran, 1,4-dioxane, dimethylformamide, methylene chloride, 1,2-dichloroethane, methanol, ethanol, acetonitrile, and the like to provide a compound of the formula (19). Alternatively, a compound of the formula (18) is reacted with hydrogen fluoride in triethylamine, optionally in a solvent such as tetrahydrofuran, 1,4-dioxane, dimethylformamide, methylene chloride, 1,2-dichloroethane, methanol, ethanol, acetonitrile, and the like to provide a compound of the formula (19). Alternatively, a compound of the formula (18) is reacted with an acid such as hydrochloric acid, sulfuric acid, trifluoroacetic acid, acetic acid, and the like, optionally in a solvent such as tetrahydrofuran, 1,4-dioxane, dimethylformamide, methylene chloride, 1,2-dichloroethane, methanol, ethanol, acetonitrile, and the like to provide a compound of the formula (19).

A compound of the formula (20) may be prepared according to the process outlined in Scheme 5.

Scheme 5:

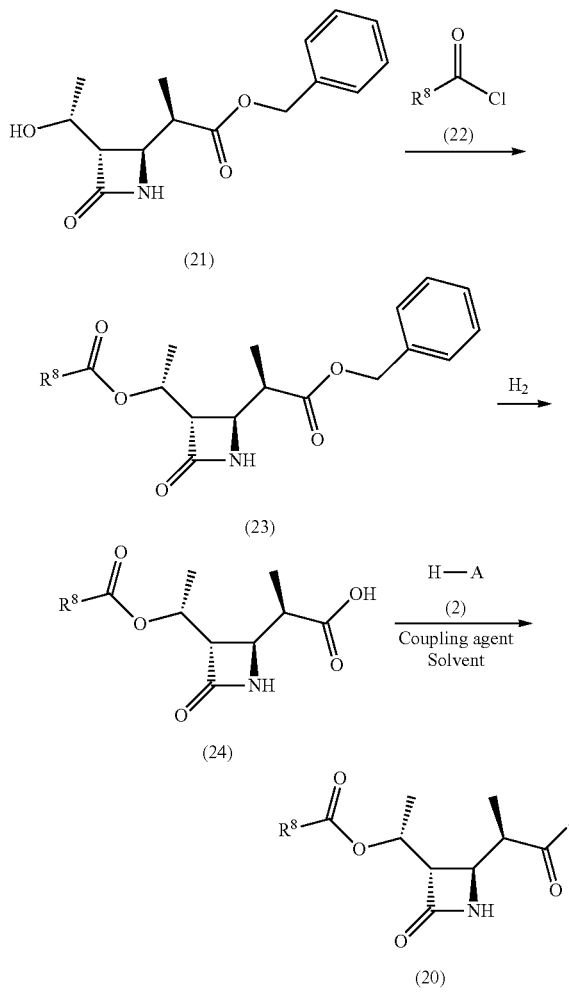

A compound of the formula (21) is reacted with a compound of the formula (22), a known compound or a compound prepared using known methods, optionally in the presence of a base such as triethylamine, diisopropylethylamine, pyridine, 2,6-lutidine, and the like, optionally in the presence of 4-N,N-dimethylaminopyridine, in an organic solvent such as tetrahydrofuran, 1,4-dioxane, dimethylformamide, methylene chloride, 1,2-dichloroethane, acetonitrile, and the like to provide a compound of the formula (23). A compound of the formula (23) is reacted with hydrogen in the presence of a palladium catalyst such as palladium on carbon, palladium acetate, palladium bis(triphenylphosphine) dichloride, palladium tetrakis(triphenylphosphine), bis(acetonitrile), and the like, in an organic solvent such as methanol, ethanol, isopropanol, ethyl acetate, tetrahydrofuran, 1,4-dioxane, and the like to provide a compound of the formula (24). A compound of the formula (24) is reacted with a compound of the formula (2), a known compound or a compound prepared using known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluorophosphate, O-(7-azabenzotriazol-1-yl)-N,N,N',N'-tetramethyl uronium hexafluorophosphate, Benzotriazole-1-yl-oxy-tris-(dimethylamino)-phosphonium hexafluorophosphate, benzotriazol-1-yl-oxytripyrrolidino-phosphonium hexafluorophosphate, 4-(4,6-dimethoxy-1,3,5-triazin-2-yl)-4-methyl morpholinium chloride and the like, in an organic solvent such as tetrahydrofuran, 1,4-dioxane, dimethylformamide, methylene chloride, 1,2-dichloroethane, methanol, ethanol, acetonitrile, and the like, optionally in the presence of a base such as triethylamine, diisopropylethylamine, pyridine, 2,6-lutidine, and the like, optionally in the presence of 4-N,N-dimethylaminopyridine, to provide a compound of the formula (20).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Bruker 400-MHz NMR. Purity (%) and mass spectral data were determined with an Agilent Technologies HPLC/MS (Zorbax SB-C18, 2.1×30 mm, 3.5 μm) with a diode array detector from 210-400 nm.

EXAMPLES

Example 1 provides methods for preparing representative compounds of formula (I). The skilled practitioner will know how to substitute the appropriate reagents, starting materials and purification methods known to those skilled in the art, in order to prepare additional compounds of the present invention.

Example 1: Synthesis of (3S,4R)-3-((R)-(1-hydroxy-ethyl)-4-((R)-[1-methyl-2-(4-methyl-piperazin-1-yl)-2-oxo-ethyl]-azetidin-2-one (MC-100093)

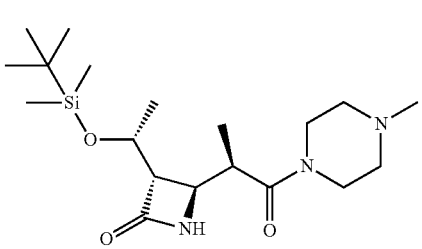 [SMILES: C[C@@H](O[Si](C)(C)C(C)(C)C)[C@H]1C(=O)N[C@@H]1[C@@H](C)C(=O)N1CCN(C)CC1]

Step 1: Synthesis of (3S,4R)-3-((R)-[1-(tert-butyl-dimethyl-silanyloxy)-ethyl]-4-((R)-[1-methyl-2-(4-methyl-piperazin-1-yl)-2-oxo-ethyl]-azetidin-2-one: To a solution of (R)-2-((2S,3S)-{3-((R)-[1-(tert-butyl-dimethyl-silanyloxy)-ethyl]-4-oxo-azetidin-2-yl}-propionic acid (10.0 g, 33.17 mmol) in dimethylformamide (200 ml) was added N,N,N',N'-tetramethyl-O-(7-azabenzotriazol-1-yl)uronium hexafluorophosphate (15.1 g, 39.8 mmol) and diethylisopropylamine (17.2 g, 132.7 mmol). After stirring at room temperature for 30 min, N-methyl piperazine (3.98 g, 39.8 mmol) was added and stirred for 18 h. The solvent was removed under vacuum. The oil remained in the flask was dissolved in 100 ml ethyl acetate and extracted with saturated aqueous NaHCO$_3$, saturated aqueous NH$_4$Cl. The organic layer was dried with anhydrous sodium sulfate and filtered. The filtrate was concentrated to oil under reduced pressure. The crude oil was purified by flash chromatography using MeOH/CH$_2$Cl$_2$ as eluent afforded (3S,4R)-3-((R)-[1-(tert-butyl-dimethyl-silanyloxy)-ethyl]-4-((R)-[1-methyl-2-(4-methyl-piperazin-1-yl)-2-oxo-ethyl]-azetidin-2-one as a light yellow solid. $^1$H NMR (400 MHz, DMSO-d6) δ 8.01 (s, 1H), 4.05 (m, 1H), 3.58 (dd, J=2.0 Hz, J=5.3 Hz, 1H), 3.48-3.49 (m, 4H) 2.94 (quint, J=7.0 Hz, 1H), 2.72

(m, 1H), 2.28 (m, 4H), 2.17 (s, 3H), 1.03 (t, J=7.0 Hz, 6H), 0.83 (s, 9H), 0.02 (s, 3H), 0.01 (s, 3H). LC/MS; M+1=384.1

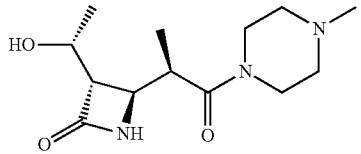 [SMILES: C[C@@H](O)[C@H]1C(=O)N[C@@H]1[C@@H](C)C(=O)N1CCN(C)CC1]

Step 2: Synthesis of (3S,4R)-3((R)-(1-Hydroxy-ethyl)-4-((R)-[1-methyl-2-(4-methyl-piperazin-1-yl)-2-oxo-ethyl]-azetidin-2-one: To a solution of 3-[1-(tert-butyl-dimethyl-silanyloxy)-ethyl]-4-[1-methyl-2-(4-methyl-piperazin-1-yl)-2-oxo-ethyl]-azetidin-2-one (3.5 g, 9.12 mmol) in 20 mL THF at 0° C. 2 mL HF/Pyridine (70%) was added and stirred for 10 min. The reaction was stirred at room temperature for 18 h. The reaction was cooled in an ice bath and quenched with Conc. NH$_4$OH to pH 7. The resulting suspension was filtered and the filtrate was purified on reverse phase 80 g C$_{18}$ column using H$_2$O/ACN as eluent afforded (0.940 g, 37%) as off white solid. $^1$H NMR (400 MHz, Methanol-d4) δ 4.01 (q, J=6.5 Hz, 1H), 3.73 (dd, J=6.8 Hz, J=2.1 Hz, 1H), 3.63 (m, 4H), 3.04 (q, J=7.1 Hz, 1H), 2.81 (dd, J=6.8, J=2.1 Hz, 1H), 2.49 (m, 2H), 2.42 (t, J=5.1 Hz, 2H) 1.22 (d, J=6.4 Hz, 3H), 1.19 (d, J=6.8 Hz, 3H). LC/MS; M+1=270.

Example 2: Synthesis of tert-butyl 4-((R)-2-((2R,3S)-3-((R)-1-hydroxyethyl)-4-oxoazetidin-2-yl)propanoyl)piperazine-1-carboxylate

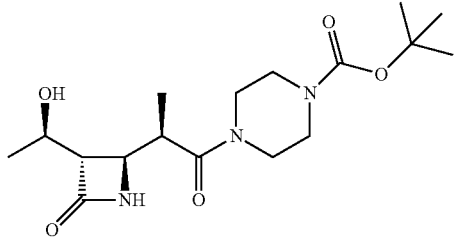 [SMILES: C[C@@H](O)[C@H]1C(=O)N[C@@H]1[C@@H](C)C(=O)N1CCN(C(=O)OC(C)(C)C)CC1]

4-{2-[3-(1-Hydroxy-ethyl)-4-oxo-azetidin-2-yl]-propionyl}-piperazine-1-carboxylic acid tert-butyl ester was prepared by the same procedure of example 1. $^1$H NMR (400 MHz, Methanol-d4) 4.03 (m, 1H), 3.74 (dd, J=7.4 Hz, J=2.1 Hz, 1H), 3.60 (m, 4H), 3.50 (m, 2H), 3.44 (m, 2H), 3.07 (m, 1H), 2.84 (dd, J=6.8 Hz, J=2.1 Hz, 1H), 1.49 (s, 9H), 1.25 (d, J=6.8 Hz, 3H), 1.21 (d, J=6.9 Hz, 3H). LC/MS; M−56=300.

Example 3: (3S,4R)-3-((R)-(1-Hydroxy-ethyl)-4-((R)-(1-methyl-2-oxo-2-piperazin-1-yl-ethyl)-azetidin-2-one

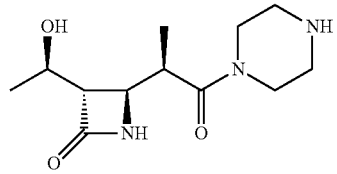 [SMILES: C[C@@H](O)[C@H]1C(=O)N[C@@H]1[C@@H](C)C(=O)N1CCNCC1]

(3S,4R)-3-((R)-(1-Hydroxy-ethyl)-4-((R)-(1-methyl-2-oxo-2-piperazin-1-yl-ethyl)-azetidin-2-one was prepared by the same procedure of example 1. $^1$H NMR (400 MHz, Methanol-d4) δ 4.45 (m, 1H), 3.64 (m, 1H), 3.40 (m, 4H), 3.2 (m, 4H), 2.65 (t, J=10.5 Hz, 1H), 2.5 (m, 1H), 1.33 (s, 3H), 1.31 (s, 3H). LC/MS; M−56=257.

Example 4: (3S,4R)-4-((R)-(1-(4-acetylpiperazin-1-yl)-1-oxopropan-2-yl)-3-((R)(1-hydroxyethyl)azetidin-2-one

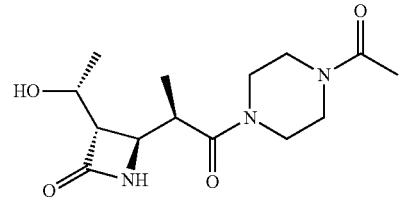 [SMILES: CC(=O)N1CCN(C(=O)[C@H](C)[C@H]2NC(=O)[C@@H]2[C@@H](C)O)CC1]

(3S,4R)-4-((R)-(1-(4-acetylpiperazin-1-yl)-1-oxopropan-2-yl)-3-((R)-(1-hydroxyethyl)azetidin-2-one was prepared by the same procedure of example 1. $^1$H NMR (400 MHz, Methanol-d4) δ 4.03 (pentaplet, J=6.5 Hz, 1H), 3.75 (dd, J=7.4 Hz, J=1.8 Hz, 1H), 3.63 (m, 8H), 3.08 (q, J=7.1 Hz, 1H), 2.86 (m, 1H), 2.15 (s, 3H), 1.24 (d, J=6.3 Hz, 3H), 1.22 (d, J=6.8 Hz, 3H). LC/MS; M+1=297.3

Example 5: (3S,4R)-4-((R)-1-(4-ethylpiperazin-1-yl)-1-oxopropan-2-yl)-3-((R)-1-hydroxyethyl)azetidin-2-one

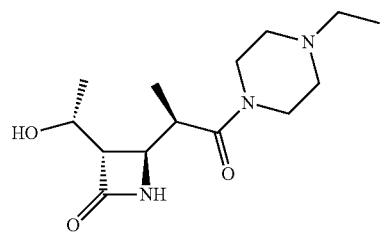 [SMILES: CCN1CCN(C(=O)[C@H](C)[C@H]2NC(=O)[C@@H]2[C@@H](C)O)CC1]

(3S,4R)-4-((R)-1-(4-ethylpiperazin-1-yl)-1-oxopropan-2-yl)-3-((R)-1-hydroxyethyl)azetidin-2-one was prepared by the same procedure of example 1. $^1$H NMR (400 MHz, CD$_3$OD) δ 4.03 (m, 1H), 3.74 (dd, J=2.0 Hz, J=7.4 Hz, 1H), 3.69 (m, 4H), 3.06 (m, 1H), 2.83 (dd, J=2.0 Hz, J=6.9 Hz, 1H), 2.71 (m, 2H), 2.65 (q, J=7.2 Hz, 2H), 2.65 (m, 4H), 1.25 (d, J=6.4 Hz, 3H), 1.21 (d, J=6.9 Hz, 3H), 1.19 (t, J=7.2 Hz, 3H); ESIMS: m/z=284.2 [(M+H)+].

Example 6: (3S,4R)-3-((R)-1-hydroxyethyl)-4-((R)-1-(4-(methylsulfonyl)piperazin-1-yl)-1-oxopropan-2-yl)azetidin-2-one

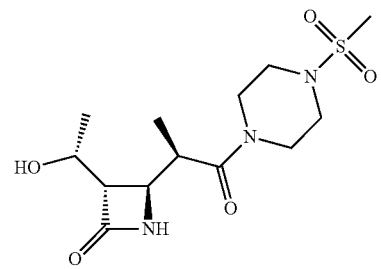 [SMILES: C[C@@H](O)[C@H]1C(=O)N[C@@H]1[C@@H](C)C(=O)N1CCN(S(C)(=O)=O)CC1]

(3S,4R)-3-((R)-1-hydroxyethyl)-4-((R)-1-(4-(methylsulfonyl)piperazin-1-yl)-1-oxopropan-2-yl)azetidin-2-one was prepared by the same procedure of example 1. ¹H NMR (400 MHz, CD₃OD) δ 4.02 (m, 1H), 3.61-3.80 (m, 5H), 3.28 (m, 2H), 3.21 (m, 2H), 3.08 (m, 1H), 2.87 (s, 3H), 2.84 (dd, J=2.1 Hz, J=6.9 Hz, 1H), 1.24 (d, J=6.3 Hz, 3H), 1.21 (d, J=6.9 Hz, 3H); ESIMS: m/z=334.1 [(M+H)+].

Example 7: (3S,4R)-4-((R)-1-(4-cyclohexylpiperazin-1-yl)-1-oxopropan-2-yl)-3-((R)-1-hydroxyethyl)azetidin-2-one

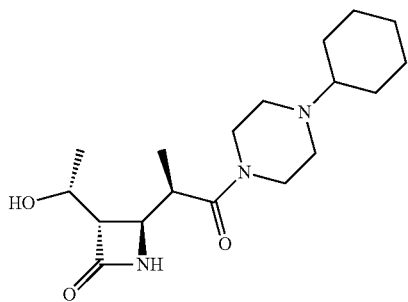 [SMILES: C[C@@H](O)[C@H]1C(=O)N[C@@H]1[C@@H](C)C(=O)N1CCN(C2CCCCC2)CC1]

(3S,4R)-4-((R)-1-(4-cyclohexylpiperazin-1-yl)-1-oxopropan-2-yl)-3-((R)-1-hydroxyethyl)azetidin-2-one as prepared by the same procedure of example 1. ¹H NMR (400 MHz, CD₃OD) δ 4.01 (m, 1H), 3.64-3.85 (m, 5H), 3.06 (m, 1H), 2.99 (m, 2H), 2.94 (m, 2H), 2.83 (dd, J=2.1 Hz, J=7.0 Hz, 1H), 2.77 (m, 1H), 2.02 (m, 2H), 1.90 (m, 2H), 1.70 (m, 1H), 1.36 (m, 5H), 1.24 (d, J=6.3 Hz, 3H), 1.21 (d, J=6.9 Hz, 3H); ESIMS: m/z=338.2 [(M+H)+].

Example 8: (3S,4R)-4-((R)-1-(4-benzoylpiperazin-1-yl)-1-oxopropan-2-yl)-3-((R)-1-hydroxyethyl)azetidin-2-one

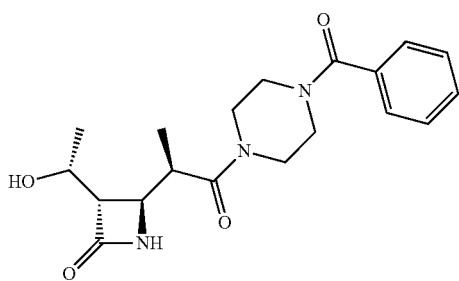 [SMILES: C[C@@H](O)[C@H]1C(=O)N[C@@H]1[C@@H](C)C(=O)N1CCN(C(=O)c2ccccc2)CC1]

(3S,4R)-4-((R)-1-(4-benzoylpiperazin-1-yl)-1-oxopropan-2-yl)-3-((R)-1-hydroxyethyl)azetidin-2-one was prepared by the same procedure of example 1. ¹H NMR (400 MHz, CD₃OD) δ 7.44-7.52 (m, 5H), 4.03 (m, 1H), 3.45-3.90 (m, 9H), 2.97-3.20 (m, 1H), 2.85 (m, 1H), 1.25 (d, J=6.4 Hz, 3H), 1.22 (d, J=6.4 Hz, 3H); ESIMS: m/z=360.2 [(M+H)+]

Example 9: (3S,4R)-3-((R)-1-hydroxyethyl)-4-((R)-1-oxo-1-(4-phenyl piperazin-1-yl)propan-2-yl)azetidin-2-one

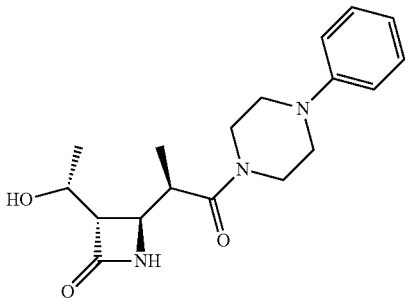 [SMILES: C[C@@H](O)[C@H]1C(=O)N[C@@H]1[C@@H](C)C(=O)N1CCN(c2ccccc2)CC1]

(3S,4R)-3-((R)-1-hydroxyethyl)-4-((R)-1-oxo-1-(4-phenylpiperazin-1-yl) propan-2-yl)azetidin-2-one was prepared by the same procedure of example 1. ¹H NMR (400 MHz, CD₃OD) δ 7.26 (m, 2H), 7.00 (d, J=7.8 Hz, 2H), 6.88 (t, J=7.3 Hz, 1H), 4.04 (m, 1H), 3.77 (m, 5H), 3.21 (q, J=5.4 Hz, J=10.6 Hz, 2H), 3.09-3.16 (m, 3H), 2.85 (dd, J=2.0 Hz, J=6.8 Hz, 1H), 1.25 (d, J=3.4 Hz, 3H), 1.23 (d, J=4.0 Hz, 3H); ESIMS: m/z=332.2 [(M+H)+].

Example 10: (3S,4R)-3-((R)-1-hydroxyethyl)-4-((R)-1-oxo-1-(4-propyl piperazin-1-yl)propan-2-yl)azetidin-2-one

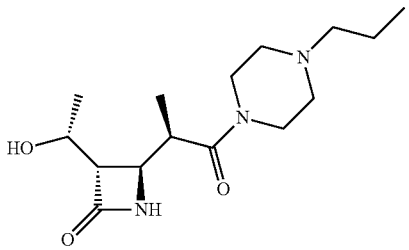 [SMILES: CCCN1CCN(C(=O)[C@H](C)[C@H]2NC(=O)[C@@H]2[C@@H](C)O)CC1]

(3S,4R)-3-((R)-1-hydroxyethyl)-4-((R)-1-oxo-1-(4-propyl piperazin-1-yl)propan-2-yl)azetidin-2-one was prepared by the same procedure of example 1. ¹H NMR (400 MHz, CD₃OD) δ 4.02 (m, 1H), 3.73 (dd, J=2.0 Hz, J=7.5 Hz, 1H), 3.61-3.66 (m, 4H), 3.04 (m, 1H), 2.81 (dd, J=2.1 Hz, J=6.8 Hz, 1H), 2.54 (m, 2H), 2.48 (t, J=5.1 Hz, 2H), 2.38 (m, 2H), 1.56 (m, 2H), 1.23 (d, J=6.3 Hz, 3H), 1.19 (d, J=7.0 Hz, 3H), 0.94 (t, J=7.4 Hz, 3H); ESIMS: m/z=298.2 [(M+H)+]

Example 11: (3S,4R)-3-((R)-1-hydroxyethyl)-4-((R)-1-(4-(4-methoxyphenyl)piperazin-1-yl)-1-oxopropan-2-yl)azetidin-2-one

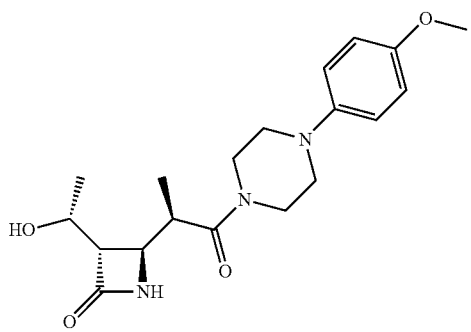 [SMILES: COc1ccc(N2CCN(C(=O)[C@H](C)[C@H]3NC(=O)[C@@H]3[C@@H](C)O)CC2)cc1]

(3S,4R)-3-((R)-1-hydroxyethyl)-4-((R)-1-(4-(4-methoxyphenyl)piperazin-1-yl)-1-oxopropan-2-yl)azetidin-2-one was prepared by the same procedure of example 1: ¹H NMR (400 MHz, CD₃OD) δ 6.97 (m, 2H), 6.85 (m, 2H), 4.03 (m, 1H), 3.73-3.77 (m, 8H), 3.01-3.13 (m, 5H), 2.84 (dd, J=2.1 Hz, J=6.8 Hz, 1H), 1.24 (d, J=5.7 Hz, 3H), 1.22 (d, J=6.2 Hz, 3H); ESIMS: m/z=362.2 [(M+H)+].

Example 12: (3S,4R)-4-((R)-1-(4-(tert-butyl)piperazin-1-yl)-1-oxopropan-2-yl)-3-((R)-1-hydroxyethyl)azetidin-2-one

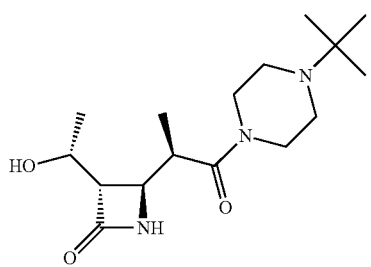 [SMILES: C[C@@H](O)[C@H]1C(=O)N[C@@H]1[C@@H](C)C(=O)N1CCN(C(C)(C)C)CC1]

(3S,4R)-4-((R)-1-(4-(tert-butyl)piperazin-1-yl)-1-oxopropan-2-yl)-3-((R)-1-hydroxyethyl)azetidin-2-one was prepared by the same procedure of example 1: ¹H NMR (400 MHz, CD₃OD) δ 4.03 (m, 1H), 3.74 (dd, J=2.0 Hz, J=7.5 Hz, 1H), 3.57-3.66 (m, 4H), 3.05 (m 1H), 2.82 (dd, J=2.1 Hz, J=6.8 Hz, 1H), 2.69 (m, 2H), 2.62 (t, J=5.2 Hz, 2H), 1.24 (d, J=6.4 Hz, 3H), 1.20 (d, J=6.9 Hz, 3H), 1.13 (s, 9H); ESIMS: m/z=312.2 [(M+H)+].

Example 13: 4-((R)-2-((2R,3S)-3-((R)-1-hydroxyethyl)-4-oxoazetidin-2-yl)propanoyl)piperazine-1-carboxamide

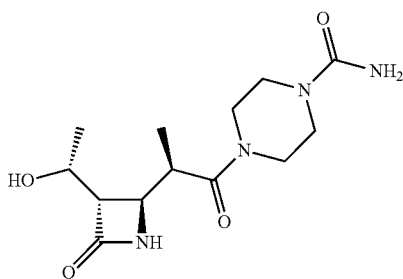 [SMILES: C[C@@H](O)[C@H]1C(=O)N[C@@H]1[C@@H](C)C(=O)N1CCN(C(N)=O)CC1]

4-((R)-2-((2R,3S)-3-((R)-1-hydroxyethyl)-4-oxoazetidin-2-yl)propanoyl)piperazine-1-carboxamide was prepared by the same procedure of example 1: ¹H NMR (400 MHz, CD₃OD) δ 4.02 (m, 1H), 3.74 (dd, J=2.0 Hz, J=7.4 Hz, 1H), 3.57-3.66 (m, 4H), 3.49 (m, 2H), 3.41 (m, 2H), 3.07 (m 1H), 2.84 (dd, J=2.1 Hz, J=6.8 Hz, 1H), 1.23 (d, J=6.4 Hz, 3H), 1.20 (d, J=6.9 Hz, 3H); ESIMS: m/z=299.2 [(M+H)+].

Example 14: (3S,4R)-3-((R)-1-hydroxyethyl)-4-((R)-1-(4-methyl-3,4-dihydro quinoxalin-1(2H)-yl)-1-oxopropan-2-yl)azetidin-2-one

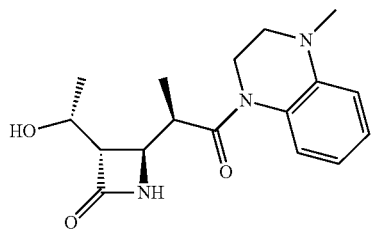 [SMILES: C[C@@H](O)[C@H]1C(=O)N[C@@H]1[C@@H](C)C(=O)N1CCN(C)c2ccccc21]

(3S,4R)-3-((R)-1-hydroxyethyl)-4-((R)-1-(4-methyl-3,4-dihydro quinoxalin-1(2H)-yl)-1-oxopropan-2-yl)azetidin-2-one was prepared by the same procedure of example 1: ¹H NMR (400 MHz, CDCl₃) δ 7.16 (t, J=7.4 Hz, 1H), 6.94 (d, J=7.7 Hz, 1H), 6.72 (d, J=8.0 Hz, 1H), 6.67 (t, J=7.6 Hz, 1H), 5.91 (s, 1H), 3.99-4.16 (m, 2H), 3.74 (m, 1H), 3.61 (m, 1H), 3.45-3.51 (m 1H), 3.32 (m, 1H), 3.22 (m, 1H), 3.10 (s, 1H), 2.96 (s, 3H), 2.61 (d, J=Hz, 1H), 1.28 (d, J=6.2 Hz, 3H), 1.17 (d, J=6.8 Hz, 3H); ESIMS: m/z=318.1 [(M+H)+]

Example 15: (R)-1-((2R,3S)-2-((R)-1-(4-methylpiperazin-1-yl)-1-oxopropan-2-yl)-4-oxoazetidin-3-yl)ethyl acetate

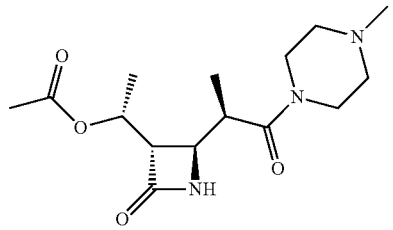 [SMILES: CC(=O)O[C@H](C)[C@H]1C(=O)N[C@@H]1[C@@H](C)C(=O)N1CCN(C)CC1]

Step 1: Synthesis of (R)-benzyl 2-((2S,3S)-3-((R)-1-acetoxyethyl)-4-oxoazetidin-2-yl)propanoate: Acetyl chloride (1.623 mmole) was added to a solution of (R)-benzyl 2-((2S,3S)-3-((R)-1-hydroxyethyl)-4-oxoazetidin-2-yl)propanoate (300 mg; 1.082 mmole) in dichloromethane (6.0 ml) and pyridine (348 uL; 4.328 mmole). This mixture was stirred at room temperature overnight. The reaction solution was diluted with dichloromethane and washed with water (2×), 1N aqueous HCl (2×), water, saturated sodium bicarbonate and brine. The organic solution was dried over anhydrous sodium sulfate, filtered and concentrated. The crude product was purified by column chromatography on silica gel using a 0 to 10% methanol in dichloromethane gradient solvent system. Pure desired (R)-benzyl 2-((2S,3S)-3-((R)-1-acetoxyethyl)-4-oxoazetidin-2-yl)propanoate was obtained as a colorless oil. 1H NMR (400 MHz, CDCl₃) δ 7.32-7.41 (m, 5H), 5.92 (s, 1H), 5.20 (m, 1H), 5.14 (s, 2H), 3.76 (dd, J=2.2 Hz, J=6.2 Hz, 1H), 3.16 (dd, J=2.1 Hz, J=7.7 Hz, 1H), 2.72 (m, 1H), 2.03 (s, 3H), 1.32 (d, J=6.3 Hz, 3H), 1.24 (d, J=7.0 Hz, 3H); ESIMS: m/z=320.1 [(M+H)+].

Step 2: Synthesis of (R)-2-((2S,3S)-3-((R)-1-acetoxyethyl)-4-oxoazetidin-2-yl)propanoic acid: (R)-benzyl 2-((2S,3S)-3-((R)-1-acetoxyethyl)-4-oxoazetidin-2-yl)propanoate was dissolved into methanol (4.0 mL). 10% palladium on carbon (20 mg) was added and this mixture was stirred under hydrogen (balloon pressure) at room temperature for 3 hours. The reaction solution was filtered through celite and concentrated down to yield 13b (58 mg; 85% yield) as a pale yellow oil. ESIMS: m/z=230.1 [(M+H)+].

Step 3: Synthesis of (R)-1-((2R,3S)-2-((R)-1-(4-methylpiperazin-1-yl)-1-oxopropan-2-yl)-4-oxoazetidin-3-yl)ethyl acetate: 4-(4,6-dimethoxy-1,3,5-triazin-2-yl)-4-methyl morpholinium chloride (14.0 mg; 0.0506 mmole) and 1-methyl piperazine (5.6 uL; 0.0506 mmole) were added sequentially to a solution of (R)-2-((2S,3S)-3-((R)-1-acetoxyethyl)-4-oxoazetidin-2-yl)propanoic acid (11.60 mg; 0.0506 mmole) in tetrahydrofuran (1.0 mL). The resulting suspension was stirred at room temperature overnight. The tan solid was filtered off and the filtrate was concentrated down. This crude product was purified by column chromatography on silica gel using a 0 to 20% methanol in dichloromethane gradient solvent system. The title compound was obtained as a colorless oil. 1H NMR (400 MHz, CD$_3$OD) δ 5.15 (m, 1H), 3.62-3.72 (m, 5H), 3.03-3.08 (m, 2H), 2.46-2.53 (m, 4H), 2.35 (s, 3H), 2.02 (s, 3H), 1.29 (d, J=6.4 Hz, 3H), 1.17 (d, J=6.8 Hz, 3H); ESIMS: m/z=312.2 [(M+H)+].

Example 16: (R)-1-((2R,3S)-2-((R)-1-(4-methylpiperazin-1-yl)-1-oxopropan-2-yl)-4-oxoazetidin-3-yl) ethyl propionate

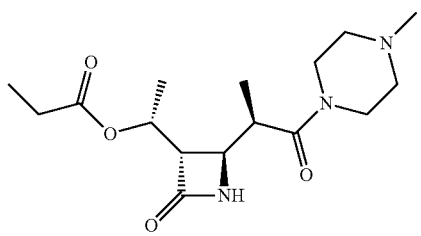 [SMILES: CCC(=O)O[C@H](C)[C@H]1C(=O)N[C@@H]1[C@@H](C)C(=O)N1CCN(C)CC1]

(R)-1-((2R,3S)-2-((R)-1-(4-methylpiperazin-1-yl)-1-oxopropan-2-yl)-4-oxoazetidin-3-yl)ethyl propionate was prepared by the same procedure of example 15: $^1$H NMR (400 MHz, CD$_3$OD) δ 5.17 (m, 1H), 3.74 (dd, J=2.1 Hz, J=7.8 Hz, 1H), 3.63-3.71 (m, 4H), 3.06 (m, 2H), 2.49-2.56 (m, 4H), 2.36 (s, 3H), 2.33 (m, 2H), 1.29 (d, J=6.4 Hz, 3H), 1.18 (d, J=6.8 Hz, 3H), 1.11 (t, J=7.5 Hz, 3H); ESIMS: m/z=326.2 [(M+H)+].

Example 17: (R)-1-((2R,3S)-2-((R)-1-(4-methylpiperazin-1-yl)-1-oxopropan-2-yl)-4-oxoazetidin-3-yl) ethyl butyrate

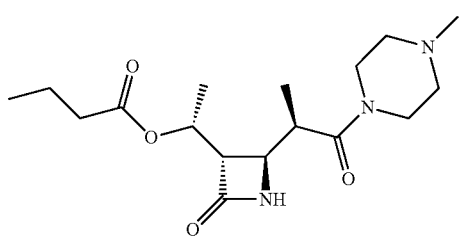 [SMILES: CCCC(=O)O[C@H](C)[C@H]1C(=O)N[C@@H]1[C@@H](C)C(=O)N1CCN(C)CC1]

(R)-1-((2R,3S)-2-((R)-1-(4-methylpiperazin-1-yl)-1-oxopropan-2-yl)-4-oxoazetidin-3-yl)ethyl butyrate was prepared by the same procedure of example 15: $^1$H NMR (400 MHz, CD$_3$OD) δ 5.18 (m, 1H), 3.74 (dd, J=2.1 Hz, J=7.7 Hz, 1H), 3.63-3.71 (m, 4H), 3.06 (m, 2H), 2.48-2.56 (m, 4H), 2.37 (s, 3H), 2.27-2.32 (m, 2H), 1.64 (m, 2H), 1.29 (d, J=6.4 Hz, 3H), 1.18 (d, J=6.8 Hz, 3H), 0.95 (t, J=7.4 Hz, 3H); ESIMS: m/z=340.2 [(M+H)+]

Example 18: (R)-1-((2R,3S)-2-((R)-1-(4-methylpiperazin-1-yl)-1-oxopropan-2-yl)-4-oxoazetidin-3-yl) ethyl isobutyrate

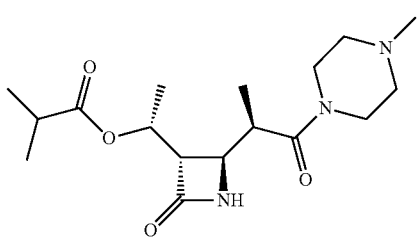 [SMILES: CC(C)C(=O)O[C@H](C)[C@H]1C(=O)N[C@@H]1[C@@H](C)C(=O)N1CCN(C)CC1]

(R)-1-((2R,3S)-2-((R)-1-(4-methylpiperazin-1-yl)-1-oxopropan-2-yl)-4-oxoazetidin-3-yl)ethyl isobutyrate was prepared by the same procedure of example 15: 1H NMR (400 MHz, CD$_3$OD) δ 5.17 (m, 1H), 3.79 (dd, J=2.2 Hz, J=7.6 Hz, 1H), 3.64-3.69 (m, 4H), 3.08 (m, 2H), 2.45-2.57 (m, 5H), 2.37 (s, 3H), 1.27 (d, J=6.4 Hz, 3H), 1.19 (d, J=6.8 Hz, 3H), 1.16 (t, J=5.6 Hz, 3H); ESIMS: m/z=340.2 [(M+H)+].

Example 19: (R)-1-((2R,3S)-2-((R)-1-(4-methylpiperazin-1-yl)-1-oxopropan-2-yl)-4-oxoazetidin-3-yl) ethyl pivalate

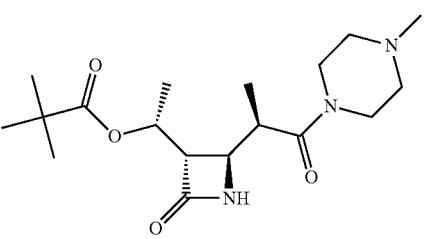 [SMILES: C[C@@H](OC(=O)C(C)(C)C)[C@H]1C(=O)N[C@@H]1[C@@H](C)C(=O)N1CCN(C)CC1]

(R)-1-((2R,3S)-2-((R)-1-(4-methylpiperazin-1-yl)-1-oxopropan-2-yl)-4-oxoazetidin-3-yl)ethyl pivalate was prepared by the same procedure of example 15: $^1$H NMR (400 MHz, CD$_3$OD) δ 5.15 (m, 1H), 3.85 (dd, J=2.1 Hz, J=7.4 Hz, 1H), 3.63-3.69 (m, 4H), 3.10 (m, 2H), 2.46-2.53 (m, 4H), 2.36 (s, 3H), 1.26 (d, J=6.5 Hz, 3H), 1.18-1.21 (m, 12H); ESIMS: m/z=354.2 [(M+H)+].

Formulations

The present invention also relates to compositions or formulations which comprise the beta lactams according to the present invention. In general, the compositions of the present invention comprise an effective amount of one or more beta lactams and salts thereof according to the present invention which are effective for providing treatment of drug addiction, drug withdrawal, related conditions, and diseases that involve modulation of glutamate uptake in their etiology; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known beta lactams. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more beta lactams according to the present invention and one or more excipients; from about 0.01 mg to about 100 mg of one or more beta lactams according to the present invention and one or more excipients; and from about 0.1 mg to about 10 mg of one or more beta lactams according to the present invention; and one or more excipients.

Procedures

The following procedures can be utilized in evaluating and selecting compounds as modulators of glutamate uptake, useful in the treatment of drug addiction, drug withdrawal, related conditions, and diseases that involve modulation of glutamate uptake in their etiology such as amyotrophic lateral sclerosis (ALS), malignant glioma, glioblastomas and glioblastoma multiforme (GBM).

Primary Cortical Astrocyte Cultures:

Astrocyte cultures were prepared according to previously established protocols (Aschner et al. 1992). Astrocytes were isolated from cerebral cortices of newborn (1-day-old) Sprague-Dawley rats. Pups were decapitated under halothane-anesthesia, and the cerebral cortices were dissected out. The meninges were removed, and the cortices were digested with bacterial neutral protease (Dispase, Invitrogen, Eugene, Oreg., USA). Astrocytes were then recovered by the repeated removal of dissociated cells and plated at a density of $1 \times 10^5$ cells/mL. Twenty-four hours after the initial plating, the media were changed to preserve the adhering astrocytes and to remove neurons and oligodendrocytes. The cultures were maintained at 37° C. in a 95% air/5% $CO_2$ incubator for 3 weeks in minimum essential medium (MEM) with Earle's salts supplemented with 10% fetal bovine serum, 100 U/mL of penicillin and 100 μg/mL of streptomycin. The media were changed twice per week. The purity of these cultures was >95%-positive for the astrocyte-specific marker, glial fibrillary acidic protein.

Glutamate Uptake Assay:

Glutamate uptake was measured as previously described (Mutkus et al. 2005), with a minor modification. Astrocytes (24-well plates) were treated with compounds in Opti-MEM reduced serum media for 30 minutes. Next, the culture media were washed 2× and replaced with the uptake buffer, pre-warmed HEPES-buffered solution containing 122 mM NaCl, 3.3 mM KCl, 0.4 mM $MgSO_4$, 1.3 mM $CaCl_2$, 1.2 mM $KH_2PO_4$, 25 mM HEPES, and 10 mM D-(+)-glucose, pH of 7.4. Five min later, pre-warmed uptake buffer containing 0.25 μCi/ml L-[$^3$H]-glutamate (specific activity: 49.0 Ci/mmol, Amersham Pharmacia Biotech, Piscataway, N.J., USA) and unlabeled glutamate at a final concentration of 100 nM (Liang et al. 2002) was added. Uptake was terminated after 10 minutes of incubation at 37° C. by three washes with ice-cold PBS, immediately followed by cell lysis in 1 mL of 1 N NaOH. An aliquot of 750 μL was neutralized in 75 μL of 10 N HCl, and radioactivity was determined by liquid scintillation counter (LS 6500, Beckman Coulter, Fullerton, Calif., USA). Protein content was determined using a 25 μL aliquot neutralized in 1 N HCl, and quantified using the bicinchoninic acid protein assay reagent kit (Pierce, Rockford, Ill., USA). Radioactivity counts were corrected for protein levels and calculated as glutamate nmol/mg protein/minute. Experiments were performed in quadruplicates in three independent cultures.

Measurement of the Extracellular L-Glutamate Concentrations

A series of experiments was carried out to determine the rate of glutamate disappearance from the media as a surrogate measure of glutamate uptake in astrocytes. Extracellular glutamate levels were measured by a fluorimetric method, using the Amplex Red Glutamic Acid assay kit (Invitrogen). Cells in 96-well plates were treated with Mn, E2 or TX in Opti-MEM media for the indicated times. Immediately thereafter, the uptake buffer containing glutamic acid (20 μM) was replaced with media in each well. After 30 minutes of incubation, 50 μL of supernatants from each sample was transferred into 96-well plates, followed by the addition of 50 μL of substrate mixture containing 100 μM Amplex Red, 0.25 U/mL horseradish peroxidase, 0.08 U/mL L-glutamate oxidase, 0.5 U/mL L-glutamatepyruvate transaminase, 200 1M L-alanine and 1·reaction buffer. After 30 min of incubation at 37° C., fluorescence was measured in a fluorescence microplate reader (FlexStation, Molecular Devices, Sunnyvale, Calif., USA) with excitation-emission at 530-590 nm.

Primary Neuron-Astrocyte Co-Culture

Primary astroglial cells were cultured from postnatal 2-3 days mouse pups. Cortices were dissected out and dissociated with papain and subsequently cultured on collagen-coated T75 flask in DMEM containing 10% fetal bovine serum (FBS). At DIV14 astrogial cells were seeded into collagen-coated 6-well plates at a concentration of $7 \times 10^5$ cells/well. Primary cortical neurons were isolated from cortices of E16 embryonic mice. After dissociated with papain, 1 million neurons were seeded per well on the top of the confluent astrocytes. Co-cultures were first maintained in Neurobasal medium supplemented with 5% FBS and 2% B-27. After 4 days half of the medium was changed into serum free Neurobasal medium supplemented with 2% B27. Cells were treated with compounds of the disclosure at DIV5 for 3-6 days accordingly.

In Vitro Screen for GLT-1 Uptake Activity in Primary Neuron-Astrocyte Co-Culture:

0.5 μM L-glutamate (cold:radioactive=99:1) and 0.3 μCi L-[$^3$H]glutamate per sample (PerkinElmer) are used for measuring glutamate uptake in mixed neuron-astrocyte cultures. Cells are first washed and pre-incubated at room temperature for 10 minutes in $Na^+$ buffer (5 mM Tris-HCl, pH 7.2, 10 mM HEPES, 140 mM NaCl, 2.5 mM KCl, 1.2 mM $CaCl_2$, 1.2 mM $MgCl_2$, 1.2 mM $K_2HPO_4$, and 10 mM D-glucose) in the presence or absence of compounds of the disclosure. Glutamate uptake reaction is started by incubating cells for 5 minutes at 37° C. in $Na^+$ buffer containing 0.5 μM L-glutamate and 0.3 μCi L-[$^3$H]glutamate per sample, followed by rapid washing twice with ice-cold $Na^+$-free assay buffer (5 mM Tris-HCl, pH 7.2, 10 mM HEPES, 140 mM Choline-Cl, 2.5 mM KCl, 1.2 mM $CaCl_2$, 1.2 mM $MgCl_2$, 1.2 mM $K_2HPO_4$, and 10 mM D-glucose). Cells are then lysed with 0.1N NaOH solution and radioactivity is measured using a scintillation counter. Protein concentrations is measured from the cell lysate using the Bradford method. Uptake data is normalized to total protein.

In Vitro Screen for XCT Activity:

U87 human glioblastoma-astrocytoma cells (ATCC number HTB14) were seeded at $0.067 \times 10^6$ cells per well and grown to confluency in 12-well plates for 6 days. On the day of the experiment, the cells were washed with pre-warmed (37° C.) sodium free uptake buffer (contents in mM: choline chloride 137.5, KCl 5.36, $KH_2PO_4$ 0.77, $MgSO_4$ 0.71, $CaCl_2$ 1.1, Glucose 10 and HEPES 10, pH 7.4) and incubated at 37° C., for 15 minutes using 80 μM L-[$^{14}$C(U)]-cysteine and at a specific activity of 1.35 μCi/1 mol in the presence and compounds of the disclosure. L-[$^{14}$C(U)]-cysteine uptake was terminated by three washes with ice-cold uptake buffer. Subsequently, cells were lysed with 0.1 N NaOH and the radioactivity in the cells measured using a liquid scintillation counter and the counts normalized to the protein contents. The data were then normalized to the 'totals' (uptake at 37° C. in the absence compounds of the disclosure) and 'blanks'

(uptake at 0° C. in the absence of compounds of the disclosure) and presented as percent inhibition ((1−(Unknown-blanks)/(totals-blanks))×100). Subsequently, the inhibitory constant at 50% inhibition (IC$_{50}$) was calculated using GraphPad Prism.

Rat Screening with Cocaine for GLT-1 Activity:

Rats were trained to self-administer intravenous cocaine (n=14) in a standard 2-lever operant chamber where each press on the active lever yielded delivery of 0.25 mg cocaine and the presentation of drug-paired cues: a stimulus light above the lever and a tone (4900 Hz). Animals underwent 12 sessions of cocaine self-administration, with a requirement of a minimum of 10 infusions attained per session. A control group (SAL; n=7) received saline infusions when their cocaine counterpart received cocaine. Following the self-administration (or yoked-saline) portion of the experiment, animals underwent extinction training, during which time presses on the previously active lever no longer resulted in cocaine or cue delivery. Animals went through extinction training for 3 weeks. For the last 6 days of extinction training (prior to sacrifice) a subset of the cocaine animals (Coc-MC; n=7) were treated with compounds of the disclosure (I.P. dosing) while the remaining subset (Coc-Veh; n=7) were injected with vehicle (sterile water; 0.3 mL). Animals were sacrificed, the nucleus accumbens core was dissected and processed to isolate a membrane-enriched fraction. Proteins were separated using 10% SDS-PAGE and transferred to PVDF membrane. The membranes were blocked in 3% milk and probed overnight at 4° C. with primary antibody against GLT-1 (1:1000, Chemicon). Membranes were washed with TBS-Tween-20 and incubated with secondary antibody at room temperature. After visualization (Pierce Western Mouse Pico Kit) band density was measured with NIH Image J software. The membranes were then re-blotted for calnexin (1:20,000; Stressgen), an endoplasmic reticulum protein used to control for the amount of protein loaded in each lane. The immunoreactivity of each GLT-1 band was normalized to calnexin and the averages within each treatment group were compared.

As indicated in FIG. 1, a significant decrease in GLT-1 protein occurs in the Cocaine-Veh group (designated Coc-Veh) relative to the saline treated group (designated Sal-Veh) (t(1,12)=5.374, p<0.05). Further, as indicated in FIG. 1, treatment of animals with 50 mg/kg daily IP dosing with MC-100093 (designated Coc-MC100093) during the last 6 days of extinction training increased GLT-1 expression relative to the Coc-Veh group.

What is claimed is:

1. A compound having formula (I):

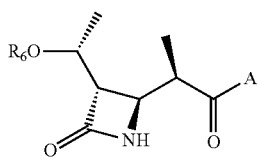

(I)

or hydrates, solvates, pharmaceutically acceptable salts thereof, wherein:

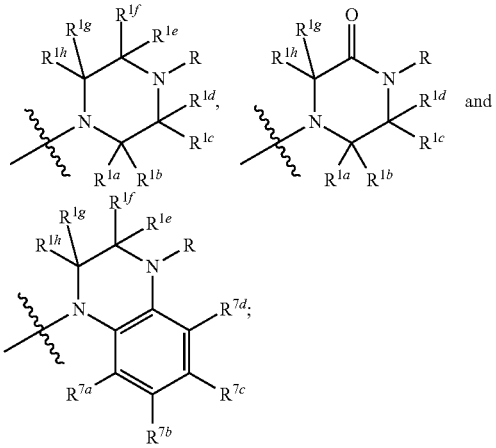

A is selected from the group consisting of

R is selected from the group consisting of hydrogen, $C_{1-6}$ linear alkyl, $C_{1-6}$ branched alkyl, optionally substituted aryl, $C(O)R^2$, $C(O)OR^3$, $C(O)NR^{4a}R^{4b}$, $SO_2R^5$, and $SO_2NH_2$;

$R^{1a}$, $R^{1b}$, $R^{1c}$, $R^{1d}$, $R^{1e}$, $R^{1f}$, $R^{1g}$ and $R^{1h}$ are each independently selected from the group consisting of hydrogen, $C_{1-6}$ linear alkyl, and $C_{1-6}$ branch alkyl;

$R^2$ is selected from the group consisting of $C_{1-6}$ linear alkyl, $C_{1-6}$ branched alkyl, and optionally substituted aryl;

$R^3$ is selected from the group consisting of $C_{1-6}$ linear alkyl, $C_{1-6}$ branched alkyl, and optionally substituted aryl;

$R^{4a}$ is selected from the group consisting of $C_{1-6}$ linear alkyl, $C_{1-6}$ branched alkyl, and optionally substituted aryl;

$R^{4b}$ is selected from the group consisting of $C_{1-6}$ linear alkyl, $C_{1-6}$ branched alkyl, and optionally substituted aryl;

$R^5$ is selected from the group consisting of $C_{1-6}$ linear alkyl, $C_{1-6}$ branched alkyl, and optionally substituted aryl;

$R^6$ is selected from the group consisting of hydrogen, $C_{1-6}$ linear alkyl, and $C(O)R^8$;

$R^{7a}$, $R^{7b}$, $R^{7c}$, and $R^{7d}$ are each independently selected from the group consisting of are each independently selected from a group consisting of hydrogen, halogen, OH, $C_{1-6}$ linear alkyl, $C_{1-6}$ branched alkyl, $C_{1-6}$ alkoxy, $C_{1-6}$ haloalkyl, $C_{1-6}$ haloalkoxy, cyano, NH($C_{1-6}$ alkyl), N($C_{1-6}$ alkyl)$_2$, NHC(O)R$^8$, C(O)NHR$^8$, C(O)N(R$^8$)$_2$, SH, S$C_{1-6}$ alkyl, SO$_2$NH$_2$, SO$_2$NHR$^8$, SO$_2$R$^8$, and NHSO$_2$R$^8$; and $R^8$ is independently selected at each occurrence from a group consisting of hydrogen, $C_{1-6}$ linear alkyl, $C_{1-6}$ branched alkyl, and $C_{3-7}$ cycloalkyl.

2. A compound according to claim 1 wherein $R^{1b}$ and $R^{1g}$ are joined together with the atoms to which they are bound to form a ring containing 5, 6, or 7 atoms.

3. A compound according to claim 1 wherein $R^{1b}$ and $R^{1f}$ are joined together with the atoms to which they are bound to form a ring containing 5, 6, or 7 atoms.

4. A compound according to claim 1 wherein $R^{1d}$ and $R^{1f}$ are joined together with the atoms to which they are bound to form a ring containing 5, 6, or 7 atoms.

5. A compound according to claim 1 wherein $R^{1b}$ and $R^{1c}$ are joined together with the atoms to which they are bound to form a ring containing 5 or 6 atoms.

6. A compound of the claim 1 that is:

(3S, 4R)-3-((R)-(1-hydroxy-ethyl)-4-((R)-[1-methyl-2-(4-methyl-piperazin-1-yl)-2-oxo-ethyl]-azetidin-2-one;

tert-butyl 4-((R)-2-((2R,3 S)-3-((R)-1-hydroxyethyl)-4-oxoazetidin-2-yl) propanoyl)piperazine-1-carboxylate;

(3S, 4R)-3-((R)-(1-Hydroxy-ethyl)-4-((R)-(1-methyl-2-oxo-2-piperazin-1-yl-ethyl)-azetidin-2-one;

(3S, 4R)-4-((R)-(1-(4-acetylpiperazin-1-yl)-1-oxopropan-2-yl)-3-((R) (1-hydroxyethyl)azetidin-2-one;

(3 S,4R)-4-((R)-1-(4-ethylpiperazin-1-yl)-1-oxopropan-2-yl)-3-((R)-1-hydroxyethyl)azetidin-2-one;

(3 S,4R)-3-((R)-1-hydroxyethyl)-4-((R)-1-(4-(methyl sulfonyl) piperazin-1-yl)-1-oxopropan-2-yl)azetidin-2-one;

(3 S,4R)-4-((R)-1-(4-cyclohexylpiperazin-1-yl)-1-oxopropan-2-yl)-3-((R)-1-hydroxyethyl)azetidin-2-one;

(3 S,4R)-4-((R)-1-(4-benzoylpiperazin-1-yl)-1-oxopropan-2-yl)-3-((R)-1-hydroxyethyl)azetidin-2-one;

(3 S,4R)-3-((R)-1-hydroxyethyl)-4-((R)-1-oxo-1-(4-phenyl piperazin-1-yl)propan-2-yl)azetidin-2-one;

(3 S,4R)-3-((R)-1-hydroxyethyl)-4-((R)-1-oxo-1-(4-propyl piperazin-1-yl)propan-2-yl)azetidin-2-one;

(3 S,4R)-3-((R)-1-hydroxyethyl)-4-((R)-1-(4-(4-methoxyphenyl) piperazin-1-yl)-1-oxopropan-2-yl) azetidin-2-one;

(3 S,4R)-4-((R)-1-(4-(tert-butyl)piperazin-1-yl)-1-oxopropan-2-yl)-3-((R)-1-hydroxyethyl)azetidin-2-one;

4-((R)-2-((2R,3 S)-3-((R)-1-hydroxyethyl)-4-oxoazetidin-2-yl)propanoyl)piperazine-1-carboxamide;

(3 S,4R)-3-((R)-1-hydroxyethyl)-4-((R)-1-(4-methyl-3,4-dihydro quinoxalin-1(2H)-yl)-1-oxopropan-2-yl)azetidin-2-one;

(R)-1-((2R,3 S)-2-((R)-1-(4-methylpiperazin-1-yl)-1-oxopropan-2-yl)-4-oxoazetidin-3-yl)ethyl acetate;

(R)-1-((2R,3 S)-2-((R)-1-(4-methylpiperazin-1-yl)-1-oxopropan-2-yl)-4-oxoazetidin-3-yl)ethyl butyrate;

(R)-1-((2R,3 S)-2-((R)-1-(4-methylpiperazin-1-yl)-1-oxopropan-2-yl)-4-oxoazetidin-3-yl)ethyl isobutyrate;

(R)-1-((2R,3 S)-2-((R)-1-(4-methylpiperazin-1-yl)-1-oxopropan-2-yl)-4-oxoazetidin-3-yl)ethyl pivalate;

or a pharmaceutically acceptable salt form thereof.

7. A composition comprising an effective amount of at least one compound according to claim 1.

8. A composition according to claim 7, further comprising at least one excipient.

9. A composition according to claim 8, wherein the at least one compound is at least one member selected from the group consisting of:

(3S, 4R)-3-((R)-(1-hydroxy-ethyl)-4-((R)-[1-methyl-2-(4-methyl-piperazin-1-yl)-2-oxo-ethyl]-azetidin-2-one;

tert-butyl 4-((R)-2-((2R,3S)-3-((R)-1-hydroxyethyl)-4-oxoazetidin-2-yl)propanoyl)piperazine-1-carboxylate;

(3S, 4R)-3-((R)-(1-Hydroxy-ethyl)-4-((R)-(1-methyl-2-oxo-2-piperazin-1-yl-ethyl)-azetidin-2-one;

(3S, 4R)-4-((R)-(1-(4-acetylpiperazin-1-yl)-1-oxopropan-2-yl)-3-((R)-(1-hydroxyethyl)azetidin-2-one;

(3 S,4R)-4-((R)-1-(4-ethylpiperazin-1-yl)-1-oxopropan-2-yl)-3-((R)-1-hydroxyethyl)azetidin-2-one;

(3 S,4R)-3-((R)-1-hydroxyethyl)-4-((R)-1-(4-(methyl sulfonyl)piperazin-1-yl)-1-oxopropan-2-yl)azetidin-2-one;

(3 S,4R)-4-((R)-1-(4-cyclohexylpiperazin-1-yl)-1-oxopropan-2-yl)-3-((R)-1-hydroxyethyl)azetidin-2-one;

(3 S,4R)-4-((R)-1-(4-benzoylpiperazin-1-yl)-1-oxopropan-2-yl)-3-((R)-1-hydroxyethyl)azetidin-2-one;

(3 S,4R)-3-((R)-1-hydroxyethyl)-4-((R)-1-oxo-1-(4-phenylpiperazin-1-yl)propan-2-yl)azetidin-2-one;

(3 S,4R)-3-((R)-1-hydroxyethyl)-4-((R)-1-oxo-1-(4-propylpiperazin-1-yl)propan-2-yl)azetidin-2-one;

(3 S,4R)-3-((R)-1-hydroxyethyl)-4-((R)-1-(4-(4-methoxyphenyl)piperazin-1-yl)-1-oxopropan-2-yl)azetidin-2-one;

(3 S,4R)-4-((R)-1-(4-(tert-butyl)piperazin-1-yl)-1-oxopropan-2-yl)-3-((R)-1-hydroxyethyl)azetidin-2-one;

4-((R)-2-((2R, 3 S)-3-((R)-1-hydroxyethyl)-4-oxoazetidin-2-yl)propanoyl)piperazine-1-carboxamide;

(3 S,4R)-3-((R)-1-hydroxyethyl)-4-((R)-1-(4-methyl-3,4-dihydroquinoxalin-1 (2H)-yl)-1-oxopropan-2-yl)azetidin-2-one;

(R)-1-((2R, 3 S)-2-((R)-1-(4-methylpiperazin-1-yl)-1-oxopropan-2-yl)-4-oxoazetidin-3-yl)ethyl acetate;

(R)-1-((2R,3 S)-2-((R)-1-(4-methylpiperazin-1-yl)-1-oxopropan-2-yl)-4-oxoazetidin-3-yl)ethyl butyrate;

(R)-1-((2R,3 S)-2-((R)-1-(4-methylpiperazin-1-yl)-1-oxopropan-2-yl)-4-oxoazetidin-3-yl)ethyl isobutyrate;

(R)-1-((2R,3 S)-2-((R)-1-(4-methylpiperazin-1-yl)-1-oxopropan-2-yl)-4-oxoazetidin-3-yl)ethyl pivalate;

and a pharmaceutically acceptable salt form thereof.

\* \* \* \* \*

UNITED STATES PATENT AND TRADEMARK OFFICE
CERTIFICATE OF CORRECTION

PATENT NO. : 9,975,879 B2
APPLICATION NO. : 14/895681
DATED : May 22, 2018
INVENTOR(S) : Magid Abou-Gharbia et al.

It is certified that error appears in the above-identified patent and that said Letters Patent is hereby corrected as shown below:

In the Specification

Column 1, under STATEMENT OF FEDERALLY FUNDED RESEARCH, the language should be changed from:
"The U.S. Government has a paid-up license in this invention and the right in limited circumstances to require the patent owner to license others on reasonable terms as provided for by the terms of grant number 5RC1DA028153-02 awarded by the National Institute on Drug Abuse."

To:
--This invention was made with government support under 5RC1DA028153-02 awarded by the National Institutes of Health. The government has certain rights in the invention.--

Signed and Sealed this
Nineteenth Day of September, 2023

Katherine Kelly Vidal
*Director of the United States Patent and Trademark Office*